United States Patent
Balsara et al.

(10) Patent No.: US 9,346,921 B2
(45) Date of Patent: May 24, 2016

(54) STYRENE-SILOXANE TRIBLOCK COPOLYMERS AS MEMBRANES FOR SELECTIVE TRANSPORT OF ALCOHOLS AND OTHER ORGANIC COMPOUNDS IN AQUEOUS MIXTURES

(71) Applicant: The Regents of the University of California, Oakland, CA (US)

(72) Inventors: Nitash P. Balsara, El Cerrito, CA (US); Ali Evren Ozcam, Woodbury, MN (US); Ashish K. Jha, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/357,541

(22) PCT Filed: Nov. 9, 2012

(86) PCT No.: PCT/US2012/064534
§ 371 (c)(1),
(2) Date: May 9, 2014

(87) PCT Pub. No.: WO2013/071174
PCT Pub. Date: May 16, 2013

(65) Prior Publication Data
US 2014/0364567 A1    Dec. 11, 2014

Related U.S. Application Data

(60) Provisional application No. 61/558,891, filed on Nov. 11, 2011.

(51) Int. Cl.
| | | |
|---|---|---|
| *C08G 77/442* | (2006.01) | |
| *B01D 71/80* | (2006.01) | |
| *B01D 61/36* | (2006.01) | |
| *B01D 69/02* | (2006.01) | |
| *B01D 69/12* | (2006.01) | |
| *B01D 61/02* | (2006.01) | |
| *B01D 61/14* | (2006.01) | |
| *B01D 71/34* | (2006.01) | |
| *B01D 71/42* | (2006.01) | |
| *B01D 71/68* | (2006.01) | |
| *C07C 29/76* | (2006.01) | |
| *C07C 45/78* | (2006.01) | |
| *C07D 307/48* | (2006.01) | |
| *B01D 71/28* | (2006.01) | |
| *B01D 71/70* | (2006.01) | |

(52) U.S. Cl.
CPC ............ *C08G 77/442* (2013.01); *B01D 61/025* (2013.01); *B01D 61/027* (2013.01); *B01D 61/145* (2013.01); *B01D 61/362* (2013.01); *B01D 69/02* (2013.01); *B01D 69/12* (2013.01); *B01D 71/34* (2013.01); *B01D 71/42* (2013.01); *B01D 71/68* (2013.01); *B01D 71/80* (2013.01); *C07C 29/76* (2013.01); *C07C 45/786* (2013.01); *C07D 307/48* (2013.01); *B01D 71/28* (2013.01); *B01D 71/70* (2013.01); *B01D 2325/20* (2013.01); *C08G 2340/00* (2013.01)

(58) Field of Classification Search
CPC ....................................................... C08G 77/442
See application file for complete search history.

(56) References Cited

U.S. PATENT DOCUMENTS

| | | | | |
|---|---|---|---|---|
| 5,700,374 A | * | 12/1997 | Steinhauser et al. | 210/640 |
| 5,945,491 A | | 8/1999 | Matyjaszewski et al. | |
| 6,111,022 A | | 8/2000 | Matyjaszewski et al. | |
| 2013/0231438 A1 | * | 9/2013 | Kim et al. | 524/500 |
| 2014/0137465 A1 | * | 5/2014 | Toste et al. | 44/438 |

FOREIGN PATENT DOCUMENTS

GB        1257304 A      12/1971

OTHER PUBLICATIONS

International Preliminary Report on Patentability received for PCT Patent Application No. PCT/US2012/064534, mailed on May 22, 2014, 10 pages.
Invitation to Pay Additional Fees received for PCT Patent Application No. PCT/US2012/064534, mailed on Mar. 14, 2013, 4 pages.
International Search Report received for PCT Patent Application No. PCT/US2012/064534, mailed on Jul. 2, 2013, 6 pages.
"1-Butanol : ICSC: 0111", IPCS INCHEM Home, 1999, 3 pages.
"2-Butanol : ICSC: 0112", IPCS INCHEM Home, 1999, 3 pages.
"Isobutanol: ICSC: 0113", IPCS INCHEM Home, 1999, 3 pages.
(Continued)

*Primary Examiner* — Margaret Moore
(74) *Attorney, Agent, or Firm* — Morrison & Foerster LLP

(57) ABSTRACT

The present disclosure relates to high molecular weight polystyrene-polydialkylsiloxane-polystyrene ("SDS") triblock copolymer compositions and methods of separating one or more organic compounds from an aqueous solution using membranes derived from SDS triblock copolymers. The methods may be used to separate the one or more organic compounds from an aqueous solution produced in a fermentation process. In some embodiments, the one or more organic compounds include an alcohol, such as, for example, ethanol. In other embodiments, the one or more organic compounds include acetone. In other embodiments, the one or more organic compounds include acetone, ethanol, and n-butanol produced in an acetone-ethanol-n-butanol (ABE) fermentation process. In other embodiments, the one or more organic compounds include one or more byproducts produced in a fermentation process.

25 Claims, 34 Drawing Sheets

(56) References Cited

OTHER PUBLICATIONS

Figure 1:
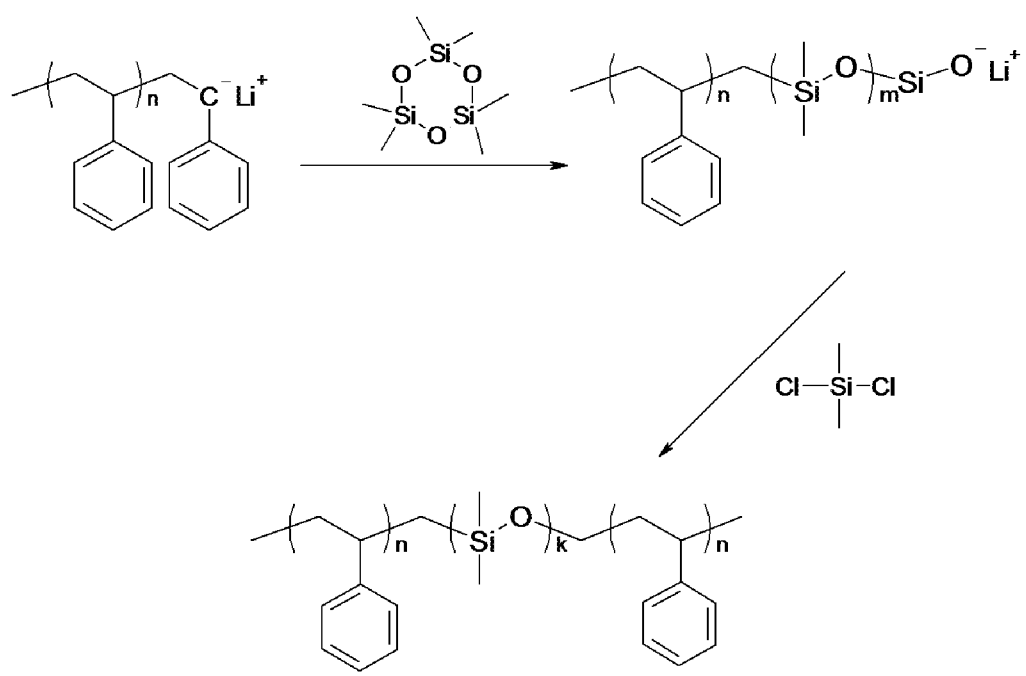

Alger et al., "The Water Solubility of 2-Butanol: A Widespread Error", Textbook Forum, vol. 68, No. 11, Nov. 1991, 1 page.
Bajaj et al., "Block Copolymers of Polystyrene and Poly(Dimethyl Siloxane). I. Synthesis and Characterization", Polymer Chemistry Edition, vol. 18, 1980, pp. 295-309.
Cavicchi et al., "Self-Diffusion and Tracer Diffusion in Sphere-Forming Block Copolymers", Macromolecules, vol. 36, No. 19, 2003, pp. 7158-7164.
Chronakis et al., "Generation of Molecular Recognition Sites in Electrospun Polymer Nanofibers via Molecular Imprinting", Macromolecules, vol. 39, No. 1, 2006, pp. 357-361.
Chu et al., "Morphologies of Strongly Segregated Polystyrene-Poly(dimethylsiloxane) Diblock Copolymers", Polymer, vol. 36, No. 8, 1995, pp. 1569-1575.
Davies et al., "Styrene-Siloxane ABA Block Copolymers Synthesis and Dilute Solution Properties", Industrial & Engineering Chemistry Product Research and Development, vol. 10, No. 2, 1971, pp. 168-171.
Dems et al., "Synthesis and Properties of Well-Defined Multiblock Copolymers: Polystyrene-Block-Polydimethylsiloxane", Makromol. Chem. vol. 192, 1991, pp. 2521-2537.
Desimone et al., "Synthesis and Bulk, Surface, and Microlithographic Characterization of Poly( 1-Butene Sulfone)-g-poly(dimethylsiloxane)", Macromolecules , vol. 24, No. 19, 1991, pp. 5330-5339.
Gaykawad et al., "Pervaporation of Ethanol from Lignocellulosic Fermentation Broth", Bioresource Technology, 2012, 36 pages.
Jha et al., "Effect of Nanoscale Morphology on Selective Ethanol Transport Through Block Copolymer Membranes", Journal of Membrane Science, vol. 373, 2011, pp. 112-120.
Lai et al., "Permselectivities of Polysiloxaneimide Membrane for Aqueous Ethanol Mixture in Pervaporation", Journal of Membrane Science, vol. 93, 1994, pp. 273-282.
Maheshwari et al., "Synthesis and Thermodynamic Properties of Poly(cyclohexylethylene-b-dimethylsiloxane-b-cyclohexylethylene)", Macromolecules, vol. 40, No. 18, 2007, pp. 6638-6646.
Miller et al., "Atom Transfer Radical Polymerization of (Meth)acrylates from Poly(dimethylsiloxane) Macroinitiators", Macromolecules, vol. 32, No. 26, 1999, pp. 8760-8767.
Miyata et al., "Morphological Effects of Microphase Separation on the Permselectivity for Aqueous Ethanol Solutions of Block and Graft Copolymer Membranes Containing Poly(dimethylsiloxane)", Macromolecules, vol. 32, No. 11, 1999, pp. 3712-3720.
Molenberg et al., "Phase Morphologies in Block Copolymers of Polystyrene and Columnar Liquid Crystalline Polydiethylsiloxane", Macromol. Chem. Phys., vol. 199, 1998, pp. 299-306.
Morgan et al., "Synthesis and Multidimensional NMR Characterization of PDMS-b-PS Prepared by Combined Anionic Ring-Opening and Nitroxide-Mediated Radical Polymerization", Macromolecules, vol. 35, No. 11, 2002, pp. 4238-4246.
Nagase et al., "Chemical Modification of Polysulphone: 2. Gas and Liquid Permeability of Polysulphone/Polydimethylsiloxane Graft Copolymer Membranes", Polymer, vol. 31, Jan. 1990, pp. 121-125.
Okamoto et al., "Pervaporation of Water—Ethanol Mixtures Through Poly-Dimethylsiloxane Block-Copolymer Membranes", Polymer Journal, vol. 19, No. 6, 1987, pp. 747-756.
Ozcam et al., "Effect of Domain Morphology and on Alcohol Pervaporation Through Polydimethylsiloxane-Containing Block Copolymer Membranes", Department of Chemical and Biomolecular Engineering, 2011, 23 pages.
Pineda et al., "Removal of Ethanolic Fermentation Inhibitors using Polydimethylsiloxane (PDMS) Membranes by Pervaporation", Rev. Ion, vol. 25, No. 1, 2012, pp. 51-59.
Rosati et al., "Synthesis of Poly(styrene-dimethylsiloxane) Block Copolymers: Influence of the Phase-Separated Morphologies on the Thermal Behaviors", Macromolecules, vol. 31, No. 13, 1998, pp. 4301-4308.
Saam et al., "Block Copolymers of Polydimethylsiloxane and Polystyrene", Macromolecules, vol. 3, No. 1, Jan.-Feb. 1970, pp. 1-4.
Saam et al., "Properties of Polystyrene-Polydimethylsiloxane Block Copolymers", Ind. Eng. Chem. Prod. Res. Develop., vol. 10, No. 1, 1971, pp. 10-14.
Takegami et al., "Pervaporation of Ethanol/water Mixtures using Novel Hydrophobic Membranes Containing Polydimethylsiloxane", Journal Membrane Science, vol. 75, 1992, pp. 93-105.
Uragami et al., "Removal of Dilute Volatile Organic Compounds in Water Through Graft Copolymer Membranes Consisting of Poly(Alkylmethacrylate) and Poly(Dimethylsiloxane) by Pervaporation and Their Membrane Morphology", Journal of Membrane Science, vol. 187, 2001, pp. 255-269.
Vaughn, Howard A., "The Synthesis and Properties of Alternating Block Polymers of Dimethylsiloxane and Bisphenol-a Carbonate", Polymer Letters, vol. 7, 1969, pp. 569-572.
Wijmans et al., "A Simple Predictive Treatment of the Permeation Process in Pervaporation", Journal of Membrane Science, vol. 79, 1993, pp. 101-113.
Wijmans et al., "The Solution-Diffusion Model: A Review", Journal of Membrane Science, vol. 107, 1995, pp. 1-21.
Zilliox et al., "Preparation and Properties of Polydimethylsiloxane and Its Block Copolymers with Styrene", Macromolecules, vol. 8, No. 5, Sep.-Oct. 1975, pp. 573-578.
Jha et al., "Master Curve Captures the Effect of Domain Morphology on Ethanol Pervaporation Through Block Copolymer Membranes", Journal of Membrane Science, vol. 401-402, 2012, pp. 125-131.

* cited by examiner (a) SB105, Feed: 8.6 wt% EtOH, Permeate: 24 wt% EtOH, $M_{SF}$: 2.88, 154 μm membrane (b) B3X4, Feed: 7.8 wt% EtOH, Permeate: 34 wt% EtOH, $M_{SF}$: 6.25, 150 μm membrane

STYRENE-SILOXANE TRIBLOCK COPOLYMERS AS MEMBRANES FOR SELECTIVE TRANSPORT OF ALCOHOLS AND OTHER ORGANIC COMPOUNDS IN AQUEOUS MIXTURES

CROSS REFERENCE TO RELATED APPLICATIONS

This is a U.S. National Phase Patent Application of PCT/US2012/064534, filed Nov. 9, 2012, which claims the benefit under 35 U.S.C. §119(e) of U.S. Provisional Application Serial No. 61/558,891 filed Nov. 11, 2011, the disclosure of which is hereby incorporated by reference in its entirety.

BACKGROUND

1. Field

The present disclosure relates generally to methods of selectively separating organic compounds from an aqueous mixture using membranes derived from copolymer compositions; more specifically it relates to methods of selectively separating one or more alcohols and/or one or more organic compounds from an aqueous mixture using membranes derived from polystyrene-polydialkylsiloxane-polystyrene triblock copolymers.

2. Related Art

Increasing concerns about global warming and decreasing amount of "easily" accessible oil reserves boosted the interest in biofuels in the last decade. The production of biofuels from renewable resources such as lignocellulosic feedstocks would allow production of fuel with no net carbon dioxide release to the atmosphere, therefore making biofuels an environmentally benign energy source. Biofuel production from lignocellulosic feedstocks consists of degradation of feedstock to fermentable sugars, fermentation of the sugars, and separation of alcohol from the fermentation broth. Conventionally, a distillation process separates the alcohol from the fermentation broth at the end of the fermentation process, but requires intensive energy resources and also suffers from azeotrope formation. Pervaporation separates biofuels from dilute aqueous solutions as an alternative technique to distillation. Since the alcohol concentration in fermentation broth is typically low (<10%), pervaporation is more economical and practical to separate the alcohol from the other components of the fermentation broth (water, sugar, bacteria and others).

Pervaporation is a membrane separation technique that is utilized to separate liquid mixtures through a membrane via a solution-diffusion mechanism. First, permeation through the membrane takes place and then the permeate is collected as a vapor on the other side of the membrane. The evaporation of the permeate on the permeate side of the membrane creates the driving force for the transfer of the permeate. The pervaporation membrane behaves as a selective barrier between the feed and the permeate; therefore, the selection of the pervaporation membrane is crucial to achieve high selectivity and fluxes. The permeability of the components through the membrane is the multiplication of their diffusion and solubility in the membrane material. For instance, for pervaporation of alcohol-water mixtures, the diffusivity of water is greater than the diffusivity of the alcohol due to the smaller dimension of the water molecule. Therefore, a membrane material with higher alcohol solubility should be selected to obtain high alcohol permselectivity.

Polydimethylsiloxane (PDMS) is well known as a membrane material for ethanol separation from dilute aqueous ethanol mixture due to its hydrophobic nature and high free volume which allows excellent selectivity and high fluxes. However, the low glass transition temperature of the polymer results in poor film-forming properties. Copolymers attracted significant attention because they can combine a variety of functional constituents into one molecule. For instance, one of the components can be chosen to promote ethanol transport while the other component provides the membrane with structural integrity. Therefore, the film forming properties of PDMS was improved by synthesis of PDMS containing copolymers for pervaporation experiments. A variety of PDMS containing graft and block copolymers containing polymethylmethacrylate (PMMA), polyalkylmethacrylates, polysulfone, polyurethaneurea, and polyimide have been synthesized and their pervaporation characteristics have been studied. Generally, mechanical properties of the block and graft PDMS copolymers as a function of temperature or molecular weight have not been quantified, and some block and graft PDMS copolymers possess poor mechanical properties unsuitable for pervaporation applications. Thus, there is a need for polymers that are highly selective for components of interest with mechanical properties suitable for membrane fabrication and/or pervaporation applications.

SUMMARY

The present disclosure relates to high molecular weight polystyrene-polydialkylsiloxane-polystyrene (hereafter "SDS") triblock copolymer compositions. In some embodiments, the present disclosure includes a poly(styrene-b-dialkylsiloxane-b-styrene) triblock copolymer including a polydialkylsiloxane block and polystyrene end blocks, wherein the triblock copolymer has a molecular weight is in the range of about 110 kg/mol to about 1000 kg/mol. In various embodiments, the triblock copolymer has a molecular weight in the range of about 110 kg/mol to about 500 kg/mol. In other embodiments, the triblock copolymer has a molecular weight in the range of about 120 kg/mol to about 300 kg/mol. In other embodiments, the triblock copolymer has a molecular weight in the range of about 130 kg/mol to about 300 kg/mol. In other embodiments, the triblock copolymer has a morphology, and the morphology is a cylindrical, lamellar, double diamond, or gyroid morphology. In other embodiments, the triblock copolymer has a morphology, and the morphology is a cylindrical or lamellar morphology. In other embodiments, the triblock copolymer has a morphology, and the morphology is a cylindrical morphology. In other embodiments, the triblock copolymer has a domain spacing (d), and the domain spacing is in the range of about 20 to about 90 nanometers. In other embodiments, the triblock copolymer loses about 5% of weight at a temperature in the range of about 290° C. to about 350° C. In other embodiments, the polydialkylsiloxane is polydimethylsiloxane. In other embodiments, the polydialkylsiloxane block has a volume fraction of about 0.6 to about 0.95 relative to the polystyrene end blocks.

The present disclosure also relates to and methods of separating one or more organic compounds from an aqueous solution using membranes derived from SDS triblock copolymers. In some embodiments, the present disclosure includes a method of selectively separating an alcohol from an aqueous mixture, the method including:

a) providing a membrane including a poly(styrene-b-dialkylsiloxane-b-styrene) triblock copolymer including a polydialkylsiloxane block and polystyrene end blocks; and b) contacting the aqueous mixture with the membrane whereby the alcohol selectively permeates through the membrane to form a permeate including the alcohol at a concentration greater than the concentration of the alcohol of the aqueous mixture. In some embodiments, the triblock copolymer has a molecular weight in the range of about 110 kg/mol to about 1000 kg/mol. In other embodiments, the triblock copolymer has a molecular weight in the range of about 110 kg/mol to about 500 kg/mol. In other embodiments, the triblock copolymer has a molecular weight in the range of about 120 kg/mol to about 300 kg/mol. In other embodiments, the triblock copolymer has a molecular weight in the range of about 130 kg/mol to about 300 kg/mol. In other embodiments, the triblock copolymer has a morphology, and the morphology is a cylindrical, lamellar, double diamond, or gyroid morphology. In other embodiments, the triblock copolymer has a morphology, and the morphology is a cylindrical or lamellar morphology. In other embodiments, the triblock copolymer has a morphology, and the morphology is a cylindrical morphology. In other embodiments, the triblock copolymer has a domain spacing (d), and the domain spacing is in the range of about 20 to about 90 nanometers. In other embodiments, the triblock copolymer loses about 5% of weight at a temperature in the range of about 290° C. to about 350° C. In other embodiments, the polydialkylsiloxane is polydimethylsiloxane. In other embodiments, the polydialkylsiloxane block has a volume fraction of about 0.6 to about 0.95 relative to the polystyrene end blocks. In other embodiments, the membrane has a separation factor ($M_{SF}$) in the range of about 1.0 to 4.0. In other embodiments, the membrane has a flux in the range of about 50 to about 600 g/m$^2$-h at about 40° C. In other embodiments, the membrane has a flux in the range of about 100 to about 800 g/m$^2$-h at about 50° C. In other embodiments, the membrane has a flux in the range of about 175 to about 1100 g/m$^2$-h at about 60° C. In other embodiments, the membrane has a flux in the range of about 200 to about 1600 g/m$^2$-h at about 70° C. In other embodiments, the membrane has a flux in the range of about 300 to about 1800 g/m$^2$-h at about 75° C. In other embodiments, the alcohol is a C2-C10 alcohol. In other embodiments, the alcohol is selected from the group consisting of ethanol, n-butanol, isobutanol, 2-butanol, 1-pentanol, 1-hexanol, 1-heptanol, 1-octanol, 1-nonanol, and 1-decanol. In other embodiments, the alcohol is ethanol. In other embodiments, the aqueous mixture includes ethanol at a concentration of about 3-75% by weight of the aqueous mixture. In other embodiments, the permeate includes ethanol at a concentration of about 20-85% by weight of the permeate. In other embodiments, the alcohol is n-butanol. In other embodiments, the aqueous mixture includes n-butanol at a concentration of about 0.5-8% by weight of the aqueous mixture. In other embodiments, the permeate includes n-butanol at a concentration of about 30-85% by weight of the permeate. In other embodiments, the alcohol is isobutanol. In other embodiments, the aqueous mixture includes isobutanol at a concentration of about 0.5-9.5% by weight of the aqueous mixture. In other embodiments, the permeate includes isobutanol at a concentration of about 20-85% by weight of the permeate. In other embodiments, the alcohol is 2-butanol. In other embodiments, the aqueous mixture includes 2-butanol at a concentration of about 0.5-12.5% by weight of the aqueous mixture. In other embodiments, the aqueous mixture further includes acetone. In other embodiments, the aqueous mixture includes acetone at a concentration of about 0.5-3% by weight of the aqueous mixture. In other embodiments, the permeate includes acetone at a concentration of about 30-55% by weight of the permeate. In other embodiments, the aqueous mixture is generated from a fermentation process.

The present disclosure also relates to membranes. In some embodiments, the present disclosure includes a membrane including the triblock copolymer of any of the SDS triblock copolymers described herein. In some embodiments, the membrane has a thickness of about 10-200 µm. In other embodiments, the membrane has a water contact angle in the range of about 105° to about 115°. In yet other embodiments, the membrane has a water contact angle of about 110°. The present disclosure also relates to thin film composite membranes, the membrane including any of the SDS triblock copolymers disclosed herein and a porous support membrane. In some embodiments, the porous support membrane is a reverse osmosis, nanofiltration, or ultrafiltration membrane. In other embodiments, the porous support membrane includes a material selected from the group consisting of polysulfone, polyacrylonitrile, and polyvinylidene fluoride.

The present disclosure also relates to methods of selectively separating one or more organic compounds from an acetone-n-butanol-ethanol (ABE) fermentation mixture. In some embodiments, the present disclosure includes a method of selectively separating one or more organic compounds from an acetone-butanol-ethanol (ABE) fermentation mixture, the method including:

c) providing a membrane including a poly(styrene-b-dialkylsiloxane-b-styrene) triblock copolymer including a polydialkylsiloxane block and polystyrene end blocks; and d) contacting the ABE fermentation mixture with the membrane whereby the alcohol selectively permeates through the membrane to form a permeate including the one or more organic compounds at a concentration greater than the concentration of the one or more organic compounds of the ABE fermentation mixture. In some embodiments, the one or more organic compounds is selected from the group consisting of acetone, n-butanol, ethanol, and mixtures of any combination thereof. In some embodiments, the triblock copolymer has a molecular weight in the range of about 110 kg/mol to about 1000 kg/mol. In some embodiments, the triblock copolymer has a molecular weight in the range of about 110 kg/mol to about 500 kg/mol. In some embodiments, the triblock copolymer has a molecular weight in the range of about 120 kg/mol to about 300 kg/mol. In some embodiments, the triblock copolymer has a molecular weight in the range of about 130 kg/mol to about 300 kg/mol. In some embodiments, the triblock copolymer has a morphology, and the morphology is a cylindrical, lamellar, double diamond, or gyroid morphology. In some embodiments, the triblock copolymer has a morphology, and the morphology is a cylindrical or lamellar morphology. In some embodiments, the triblock copolymer has a morphology, and the morphology is a cylindrical morphology. In some embodiments, the triblock copolymer has a domain spacing (d), and the domain spacing is in the range of about 20 to about 90 nanometers. In some embodiments, the triblock copolymer loses about 5% of weight at a temperature in the range of about 290° C. to about 350° C. In some preferred embodiments, the polydialkylsiloxane is polydimethylsiloxane. In some embodiments, the polydialkylsiloxane block has a volume fraction of about 0.6 to about 0.95 relative to the polystyrene end blocks.

The present disclosure also relates to methods of selectively separating one or more organic compounds from an aqueous mixture. In some embodiments, the present disclosure includes a method of selectively separating one or more organic compounds from an aqueous mixture, the method including:

e) providing a membrane including a poly(styrene-b-dialkylsiloxane-b-styrene) triblock copolymer including a polydialkylsiloxane block and polystyrene end blocks; and f) contacting the aqueous mixture with the membrane whereby the one or more organic compounds selectively permeates through the membrane to form a permeate including the one or more organic compounds at a concentration greater than the concentration of the one or more organic compounds of the aqueous mixture. In some embodiments, the one or more organic compounds is selected from the group consisting of acetone, ethanol, n-butanol, isobutanol, 2-butanol, 1-pentanol, 1-hexanol, 1-heptanol, 1-octanol, 1-nonanol, 1-decanol, acetic acid, formic acid, levulinic acid, succinic acid, furfural, 5-hydroxymethylfurfural, 2-furoic acid, vanillic acid, ferulic acid, p-coumaric acid, syringic acid (4-hydroxy-3,5-dimethoxybenzoic acid), 4-hydroxybenzoic acid; protocatechuic acid (3,4-dihydroxybenzoic acid); homovanillic acid (2-(4-hydroxy-3-methoxy-phenyl)acetic acid); caffeic acid (3,4-dihydroxycinnamic acid); sinapic acid; propionic acid; vanillylmandelic acid; 4-hydroxymandelic acid; 4-hydroxyphenylacetic acid; 3-hydroxybenzoic acid; 2,5-dihydroxybenzoic acid; benzoic acid; vanillin; syringaldehyde; 4-hydroxybenzaldehyde; coniferyl aldehyde (4-OH-3-OCH$_3$-cinnamaldehyde); sinapinaldehyde (3,5-dimethoxy-4-hydroxycinnamaldehyde); protocatechualdehyde (3,4-dihydroxybenzaldehyde); acetovanillone (4'-hydroxy-3'-methoxyacetophenone); acetosyringone (3',5'-dimethoxy-4'-hydroxyacetophenone); guaiacol; coniferyl alcohol (4-(3-hydroxy-1-propenyl)-2-methoxyphenol); hydroquinone; catechol (pyrocatechol); vanillyl alcohol (4-hydroxy-3-methoxybenzyl alcohol); eugenol; and mixtures of any combination thereof. In some embodiments, the one or more organic compounds is selected from the group consisting of acetone, ethanol, n-butanol, isobutanol, 2-butanol, 1-pentanol, 1-hexanol, 1-heptanol, 1-octanol, 1-nonanol, and 1-decanol and mixtures of any combination thereof. In some embodiments, the one or more organic compounds is selected from the group consisting of acetic acid, formic acid, levulinic acid, succinic acid, furfural, 5-hydroxymethylfurfural, and mixtures of any combination thereof. In some embodiments, the one or more organic compounds is 5-hydroxymethylfurfural. In some embodiments, the one or more organic compounds is furfural. In some embodiments, the triblock copolymer has a molecular weight in the range of about 110 kg/mol to about 1000 kg/mol. In some embodiments, the triblock copolymer has a molecular weight in the range of about 110 kg/mol to about 500 kg/mol. In some embodiments, the triblock copolymer has a molecular weight in the range of about 120 kg/mol to about 300 kg/mol. In some embodiments, the triblock copolymer has a molecular weight in the range of about 130 kg/mol to about 300 kg/mol. In some embodiments, the triblock copolymer has a morphology, and the morphology is a cylindrical, lamellar, double diamond, or gyroid morphology. In some embodiments, the triblock copolymer has a morphology, and the morphology is a cylindrical or lamellar morphology. In some embodiments, the triblock copolymer has a morphology, and the morphology is a cylindrical morphology. In some embodiments, the triblock copolymer has a domain spacing (d), and the domain spacing is in the range of about 20 to about 90 nanometers. In some embodiments, the triblock copolymer loses about 5% of weight at a temperature in the range of about 290° C. to about 350° C. In some embodiments, the polydialkylsiloxane is polydimethylsiloxane. In some embodiments, the polydialkylsiloxane block has a volume fraction of about 0.6 to about 0.95 relative to the polystyrene end blocks. In some embodiments, the one or more organic compounds is a byproduct of a fermentation reaction.

DESCRIPTION OF DRAWING FIGURES

FIG. 1. Reaction scheme of SDS triblock copolymers via sequential anionic polymerization of styrene and hexamethylcyclotrisiloxane and subsequent coupling with dichlorodimethylsilane.

Figure 2:
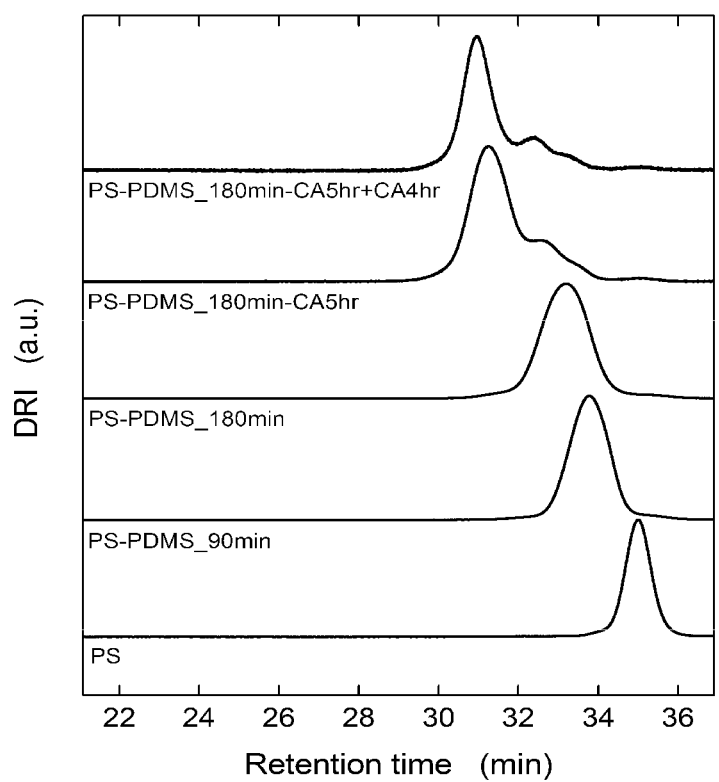

FIG. 2. GPC chromatographs for polystyrene (PS), a polystyrene-b-polydimethylsiloxane (PS-b-PDMS) diblock copolymer, and the resulting SDS triblock copolymer after coupling with dichlorodimethylsilane.

Figure 3:
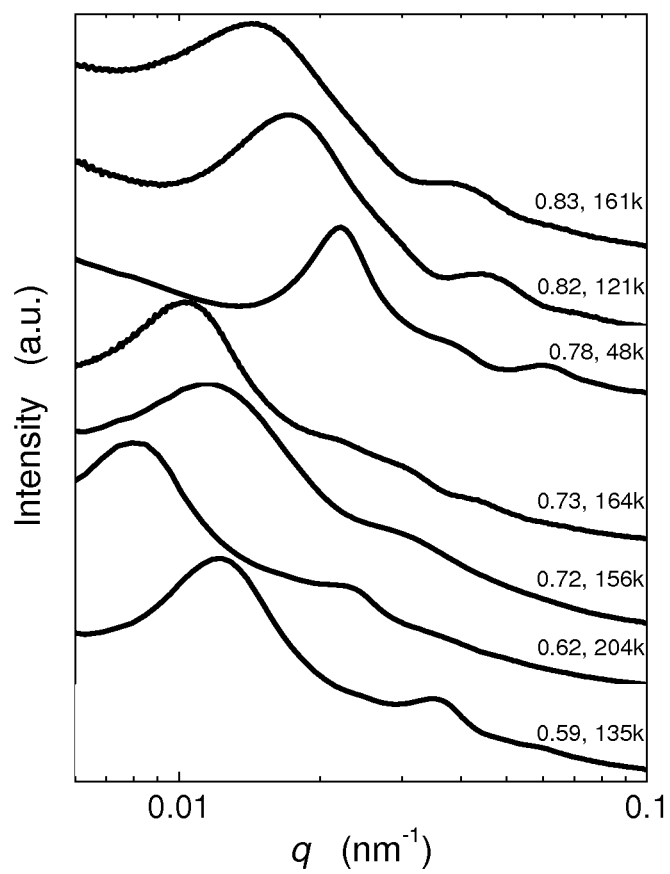

FIG. 3. SAXS profiles of SDS triblock copolymers.

Figure 4:
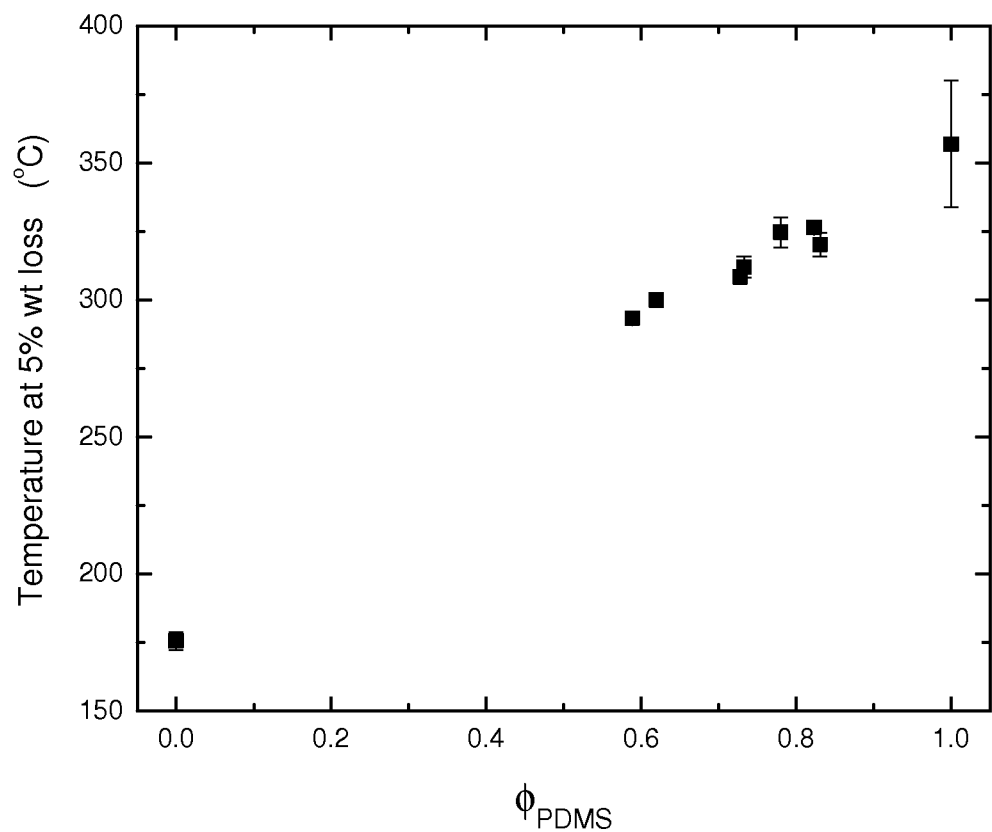

FIG. 4. Stability of SDS triblock copolymers as a function of PDMS volume fraction.

Figure 5:
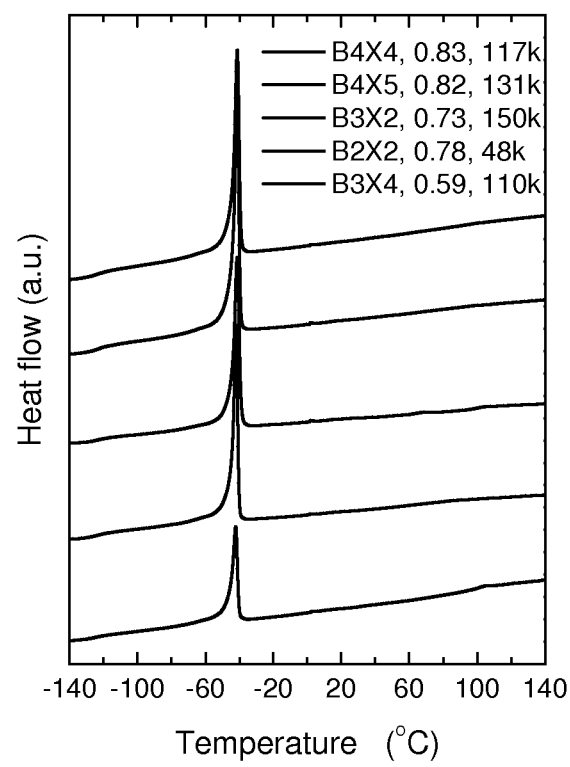

FIG. 5. DSC thermograms of SDS triblock copolymers.

Figure 6:
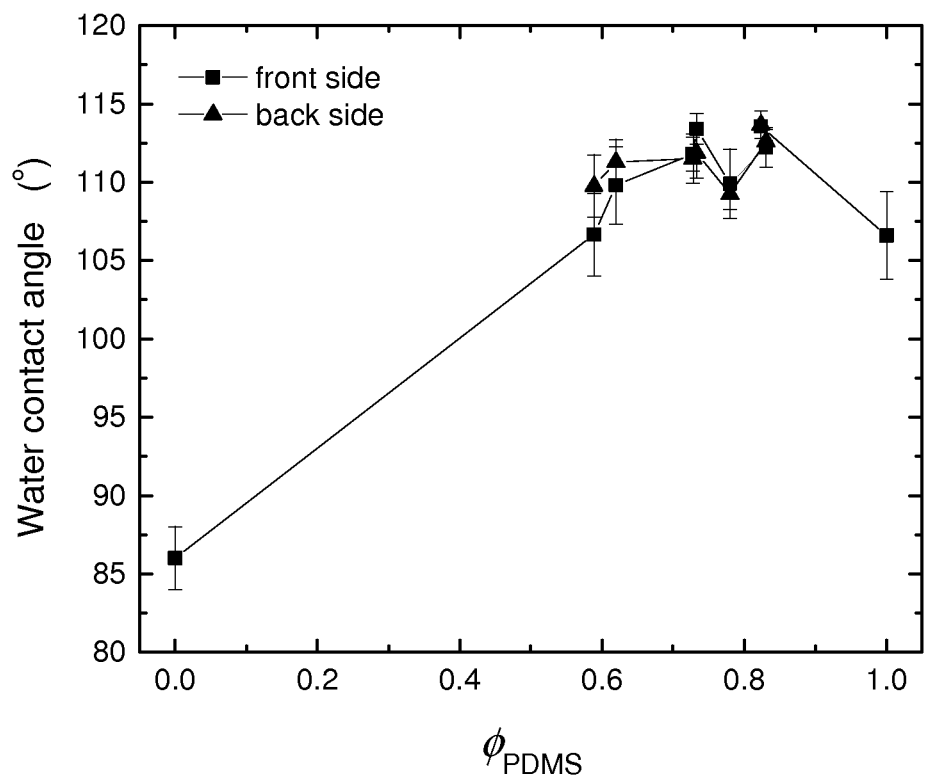

FIG. 6. Wettability behavior of SDS membranes as a function of PDMS volume fraction.

Figure 7:
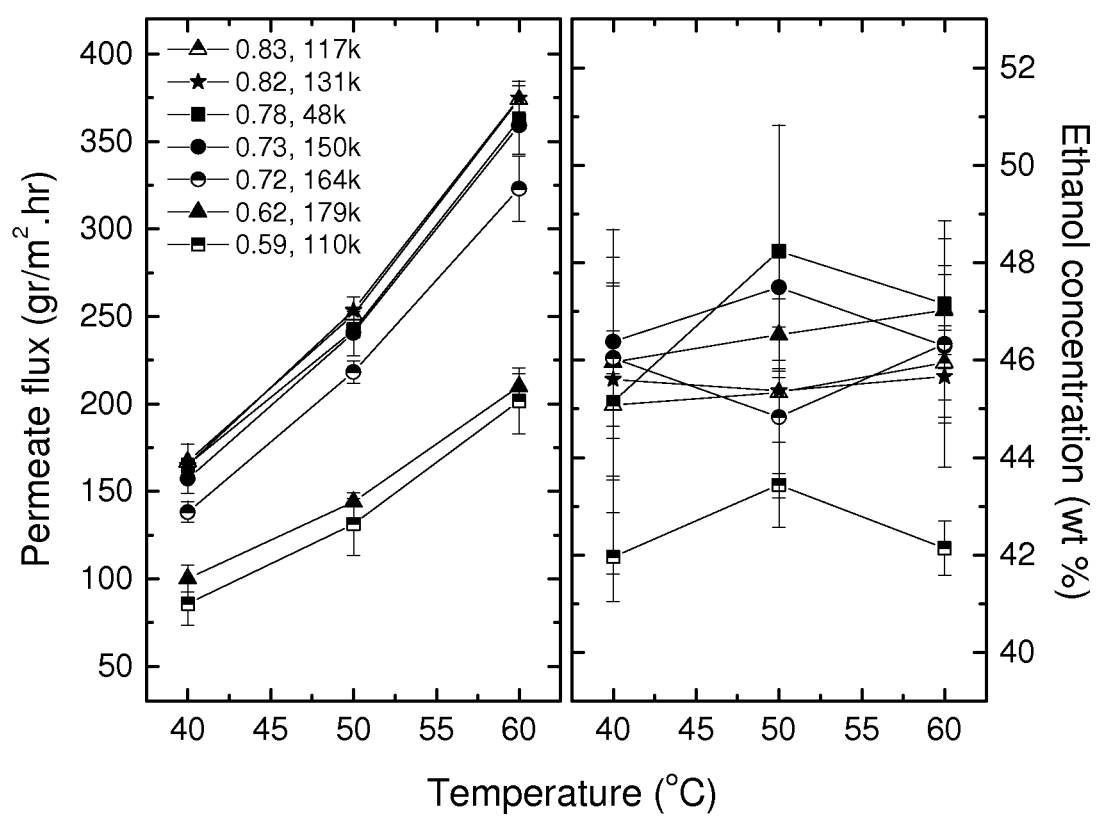

FIG. 7. The permeate flux and ethanol concentration in the permeate as a function of temperature for SDS copolymers with different compositions and molecular weights for 8% (w/w) ethanol concentration in the feed.

Figure 8:
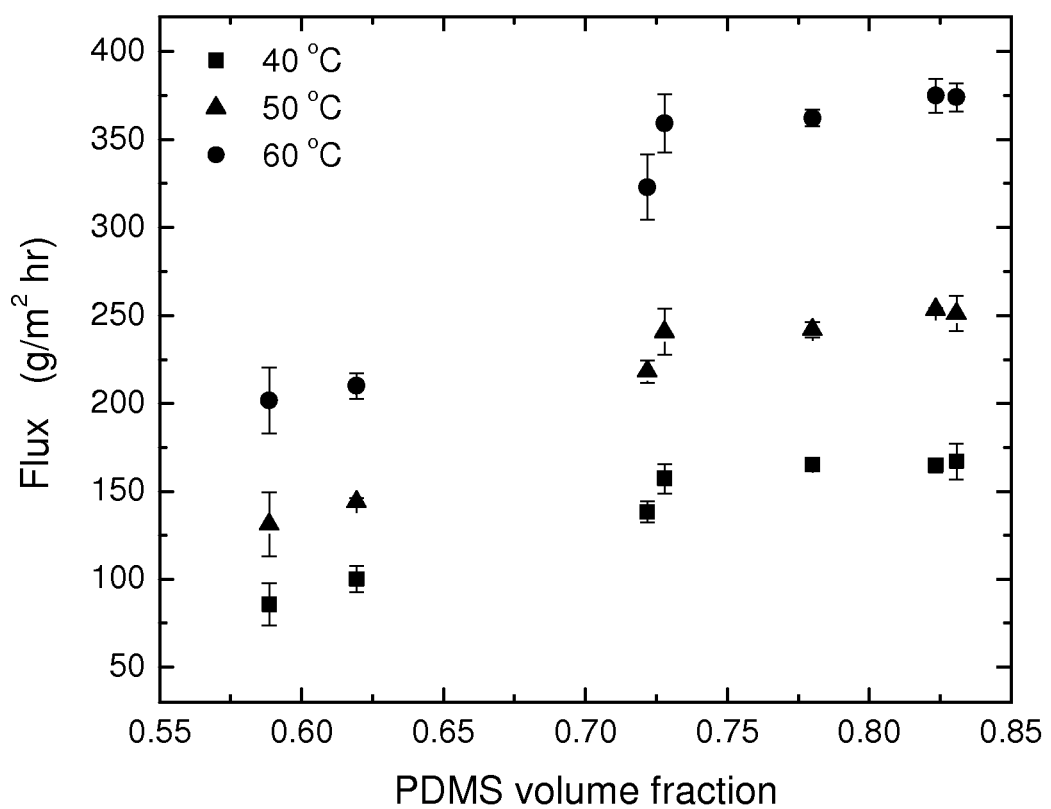

FIG. 8. Flux of permeate from 8% (w/w) ethanol feed through SDS membranes as a function of PDMS volume fraction at 40 (■), 50 (▲), and 60 (•)° C.

Figure 9:
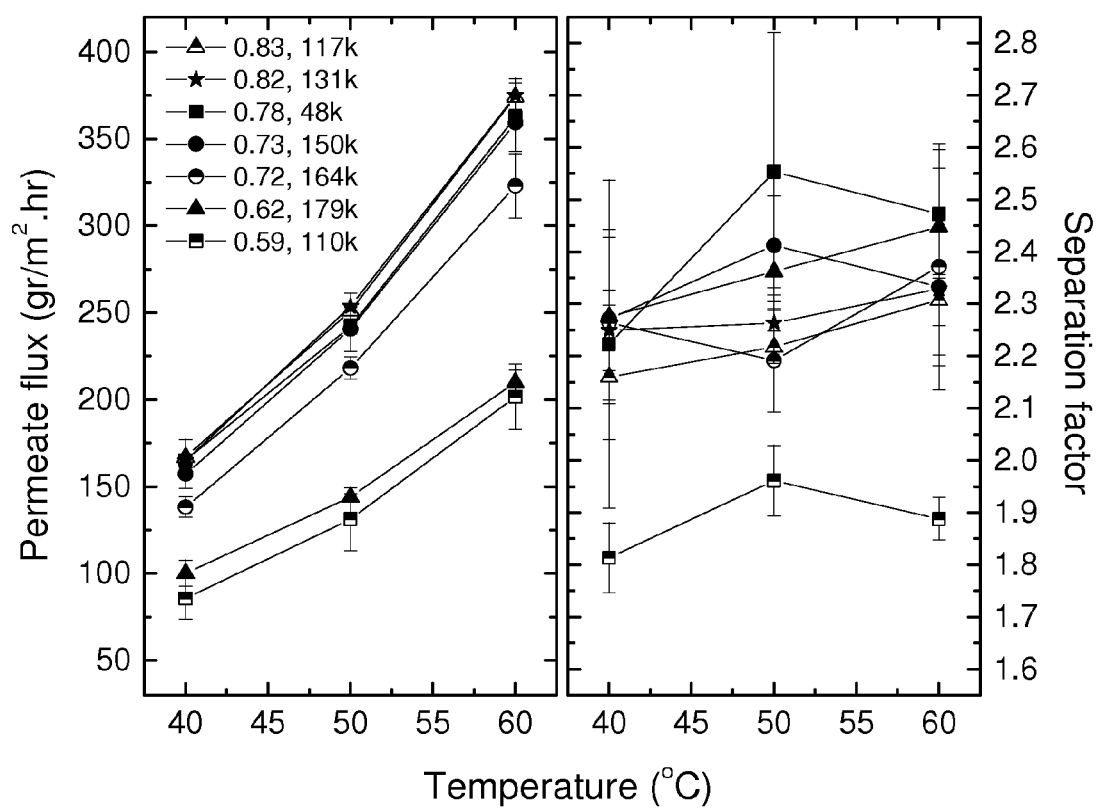

FIG. 9. Permeate flux and membrane separation factor as a function of temperature for SDS copolymers with different composition and molecular weights for 8% (w/w) ethanol concentration in the feed.

Figure 10:
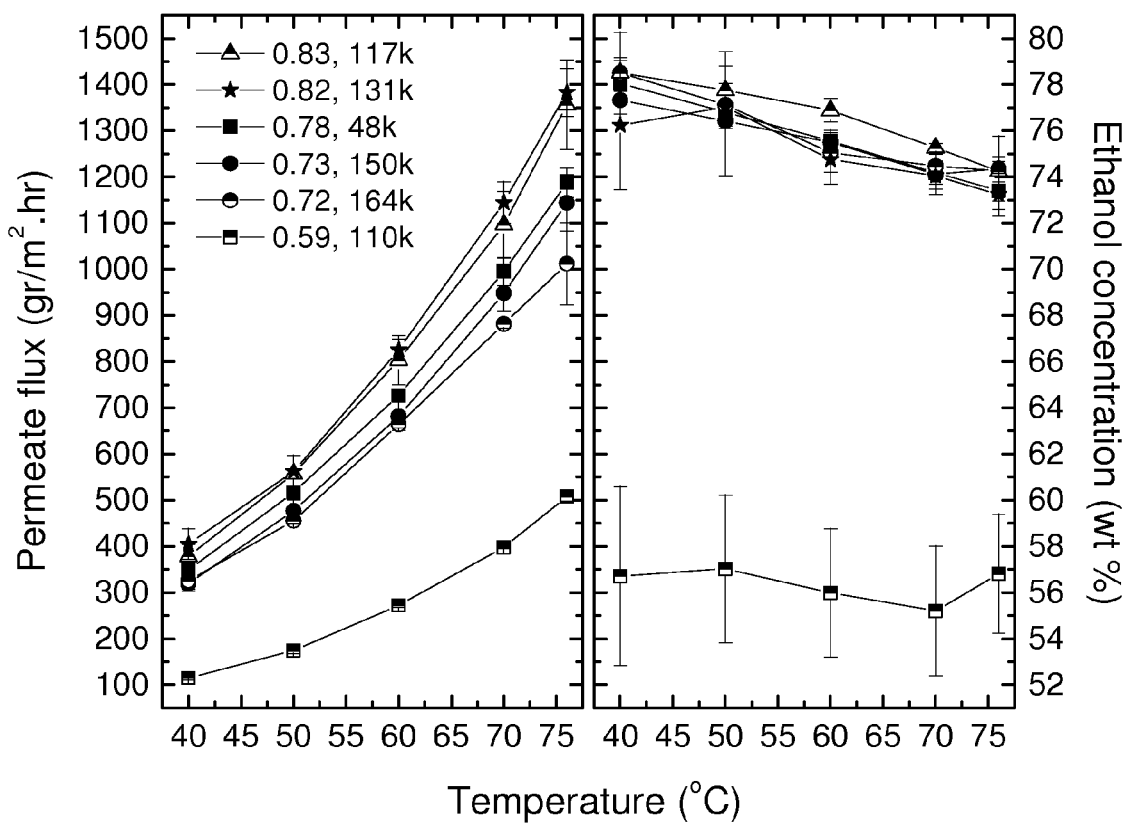

FIG. 10. The permeate flux and ethanol concentration in the permeate as a function of temperature for SDS copolymers with different composition and molecular weights for 45% (w/w) ethanol concentration in the feed.

Figure 11:
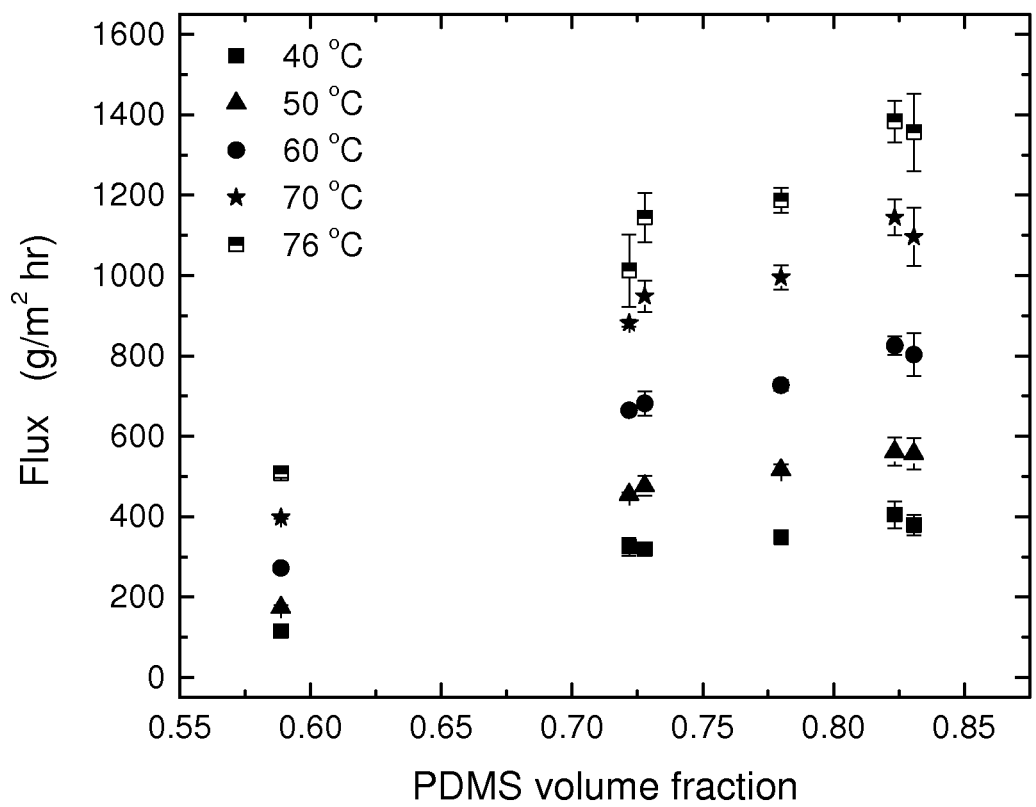

FIG. 11. Flux of permeate from 8% (w/w) ethanol feed through SDS membranes as a function of PDMS volume fraction at 40 (■), 50 (▲), 60 (•), 70 (★), and 76° C. (■).

Figure 12:
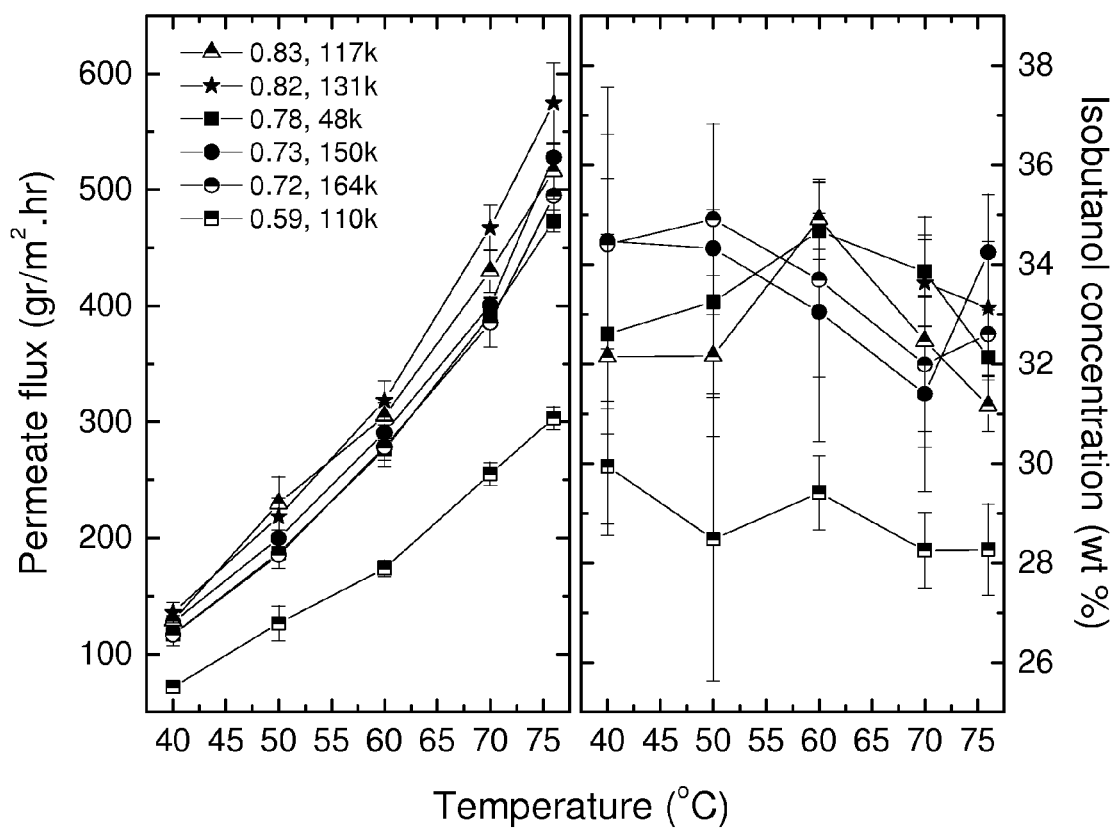

FIG. 12. Flux and isobutanol concentration in the permeate as a function of temperature for SDS copolymers with different compositions and molecular weights for 1% (w/w) isobutanol concentration in the feed.

Figure 13:
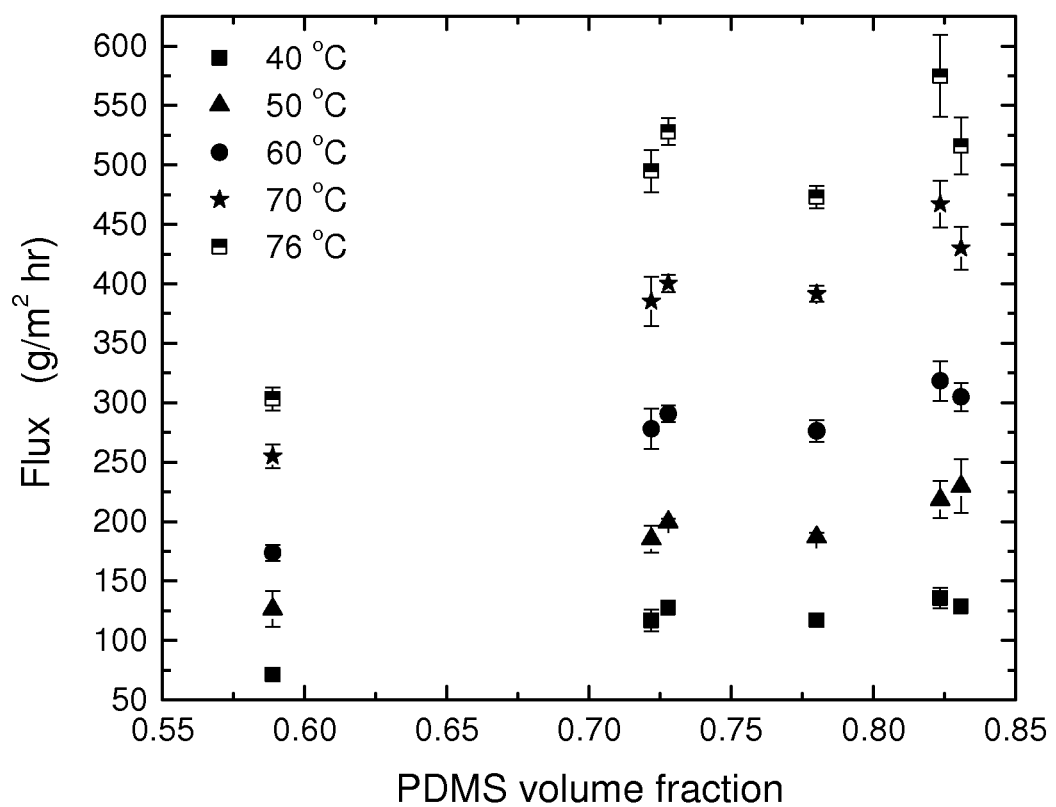

FIG. 13. Flux of permeate from 1% (w/w) isobutanol feed through SDS membranes as a function of PDMS volume fraction at 40 (■), 50 (▲), 60 (•), 70 (★), and 76° C. (■).

Figure 14:
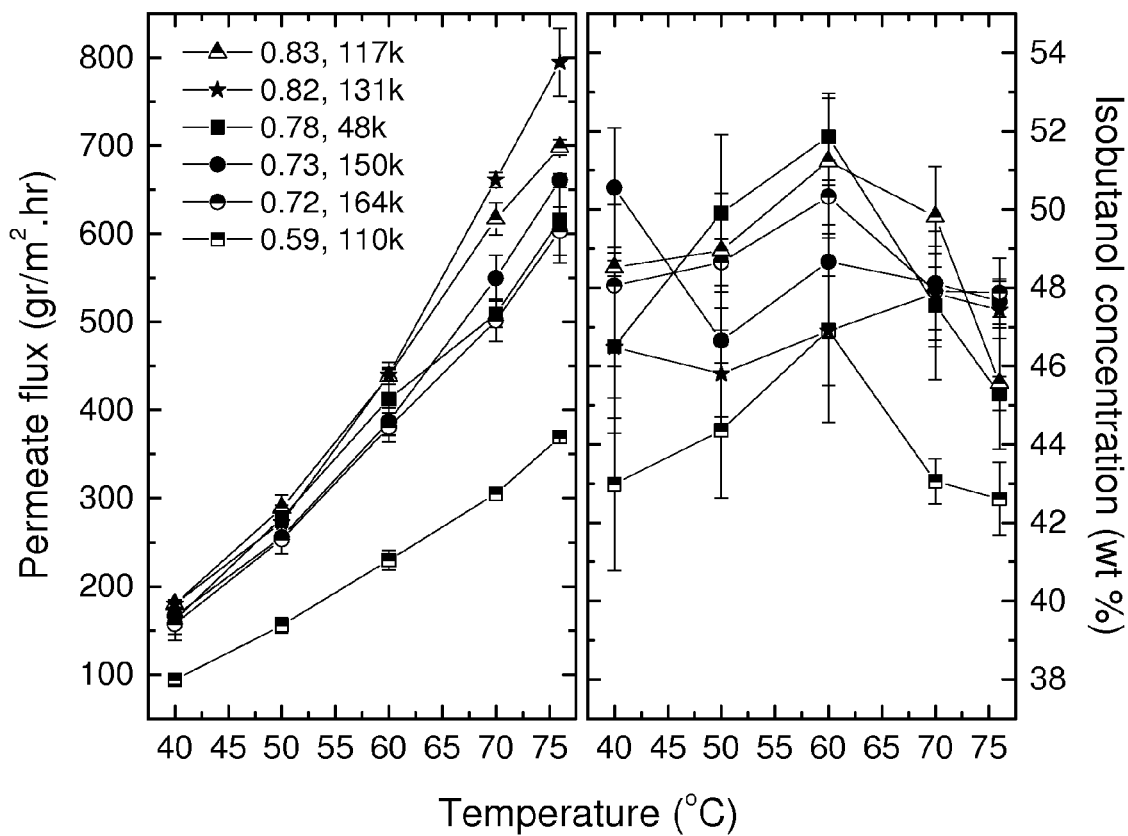

FIG. 14. Flux and isobutanol concentration in the permeate as a function of temperature for SDS copolymers with different compositions and molecular weights for 2% (w/w) isobutanol concentration in the feed.

Figure 15:
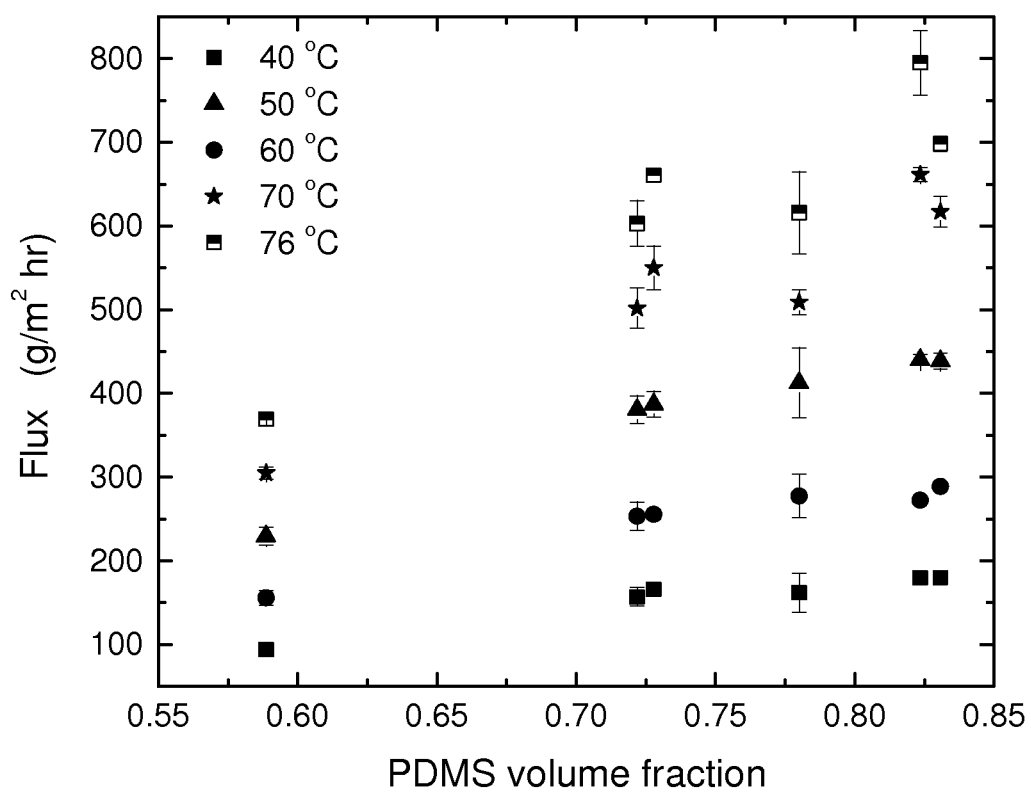

FIG. 15. Flux of permeate from 2% (w/w) isobutanol feed through SDS membranes as a function of PDMS volume fraction at 40 (■), 50 (▲), 60 (•), 70 (★), and 76° C. (■).

Figure 16:
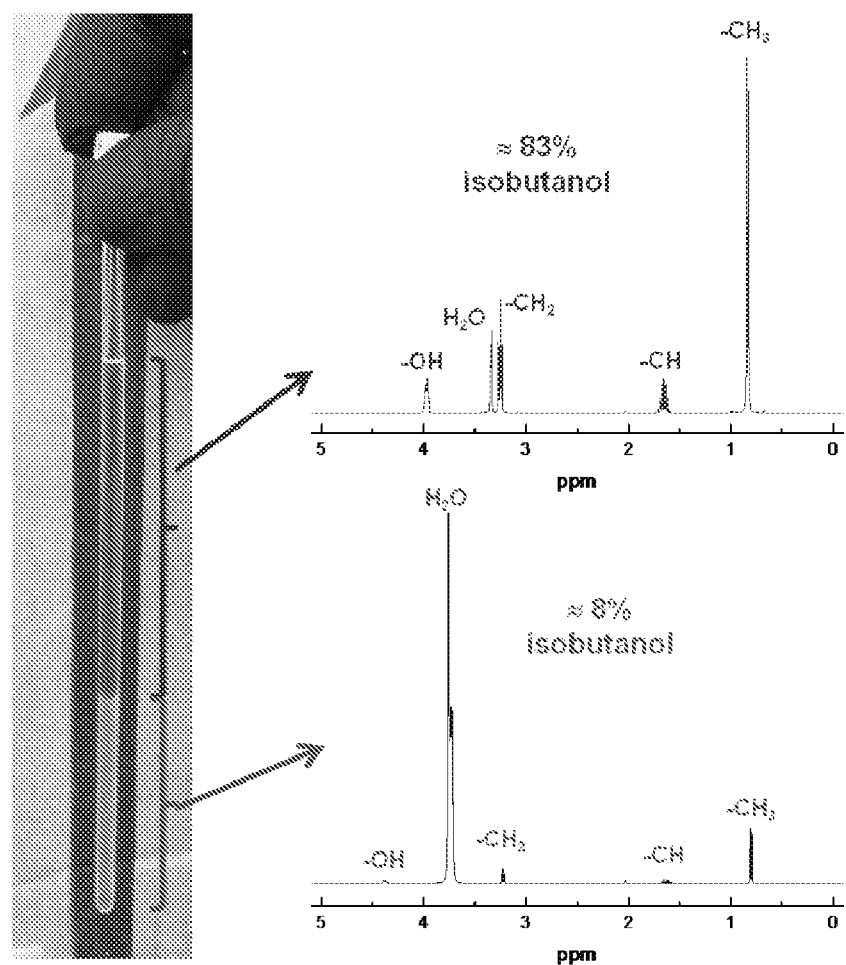

FIG. 16. The permeate obtained through SDS membrane from the feed with a composition of 2% (w/w) isobutanol. The low solubility of isobutanol in water resulted in phase separation. The top isobutanol-rich and bottom water-rich phases have compositions of 83 and 8% (w/w) isobutanol composition, respectively.

Figure 17:
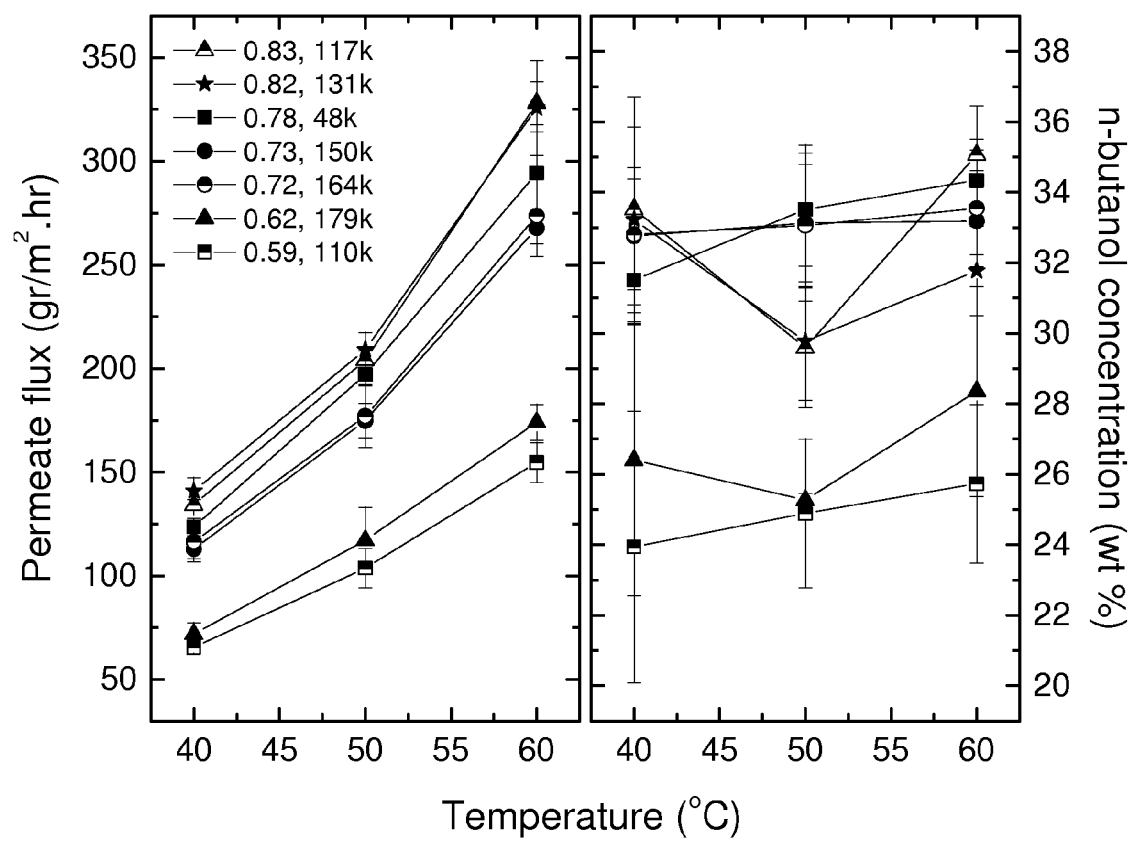

FIG. 17. Flux and n-butanol concentration in the permeate as a function of temperature for SDS copolymers with different compositions and molecular weights for 1% (w/w) n-butanol concentration in the feed.

Figure 18:
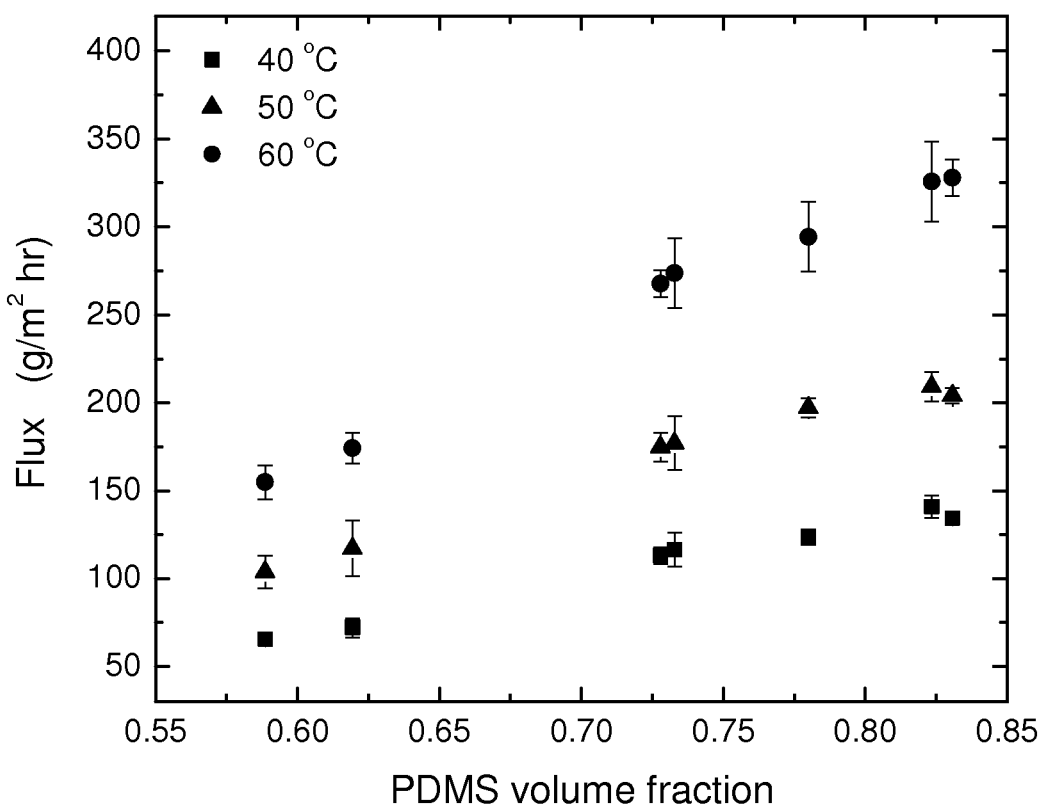

FIG. 18. Flux of permeate from 1% (w/w) n-butanol feed through SDS membranes as a function of PDMS volume fraction at 40 (■), 50 (▲), and 60(•)° C.

Figure 19:
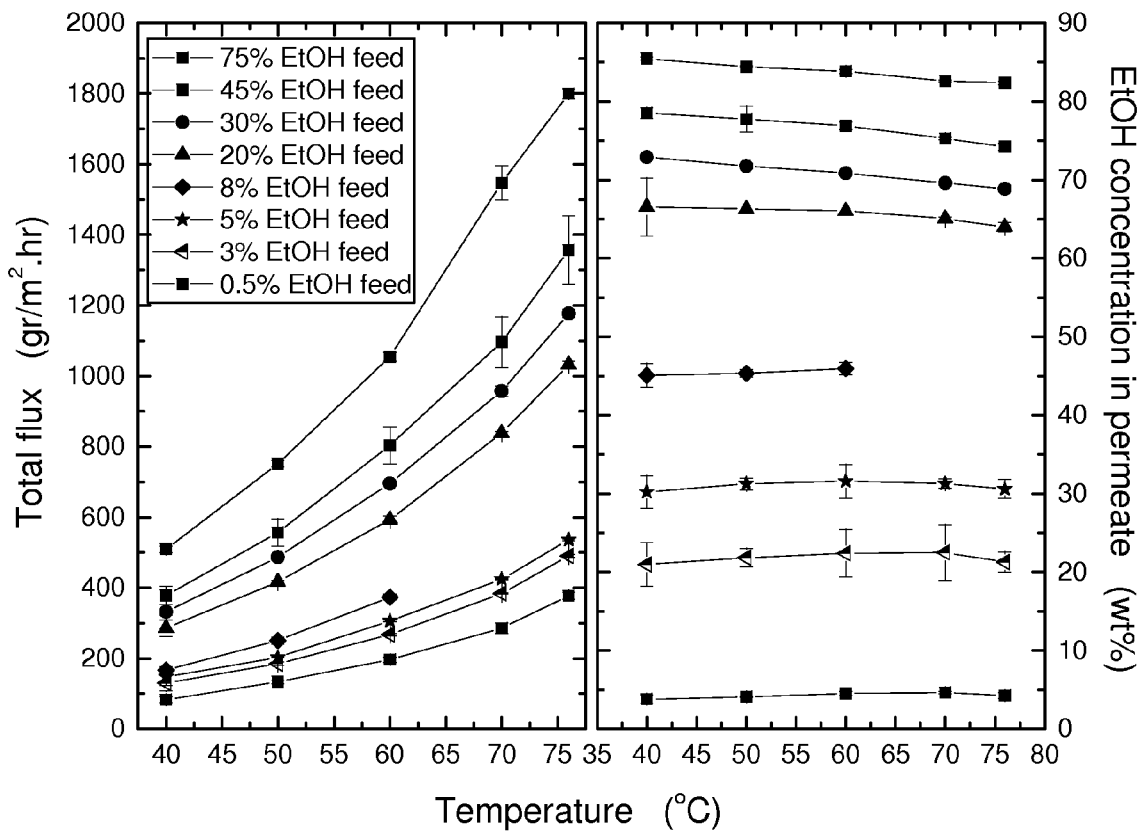

FIG. 19. Flux as a function of temperature is plotted for different ethanol feed compositions (B4X4 membrane, 0.83 PDMS volume fraction).

Figure 20:
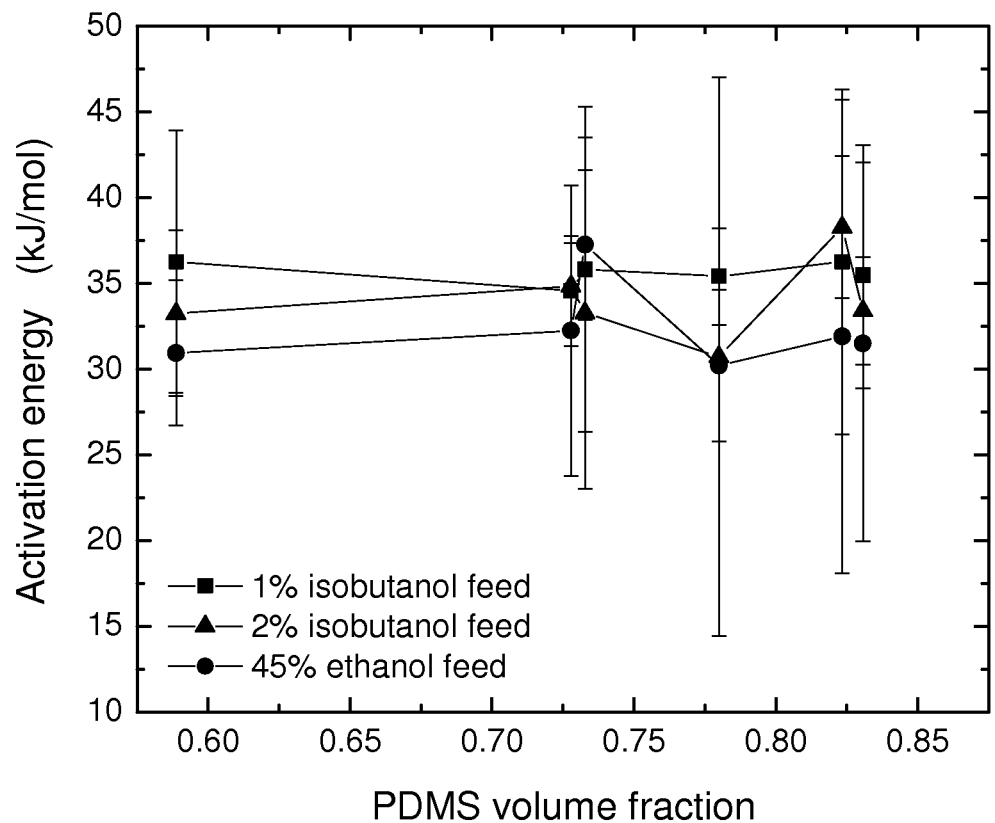

FIG. 20. Activation energies calculated with Arrhenius Equation for the effect of temperature on flux for 1 (■) and 2% (▲) isobutanol and 45% ethanol (•) (w/w) feeds as a function of PDMS volume fraction for SDS copolymers.

Figure 21:
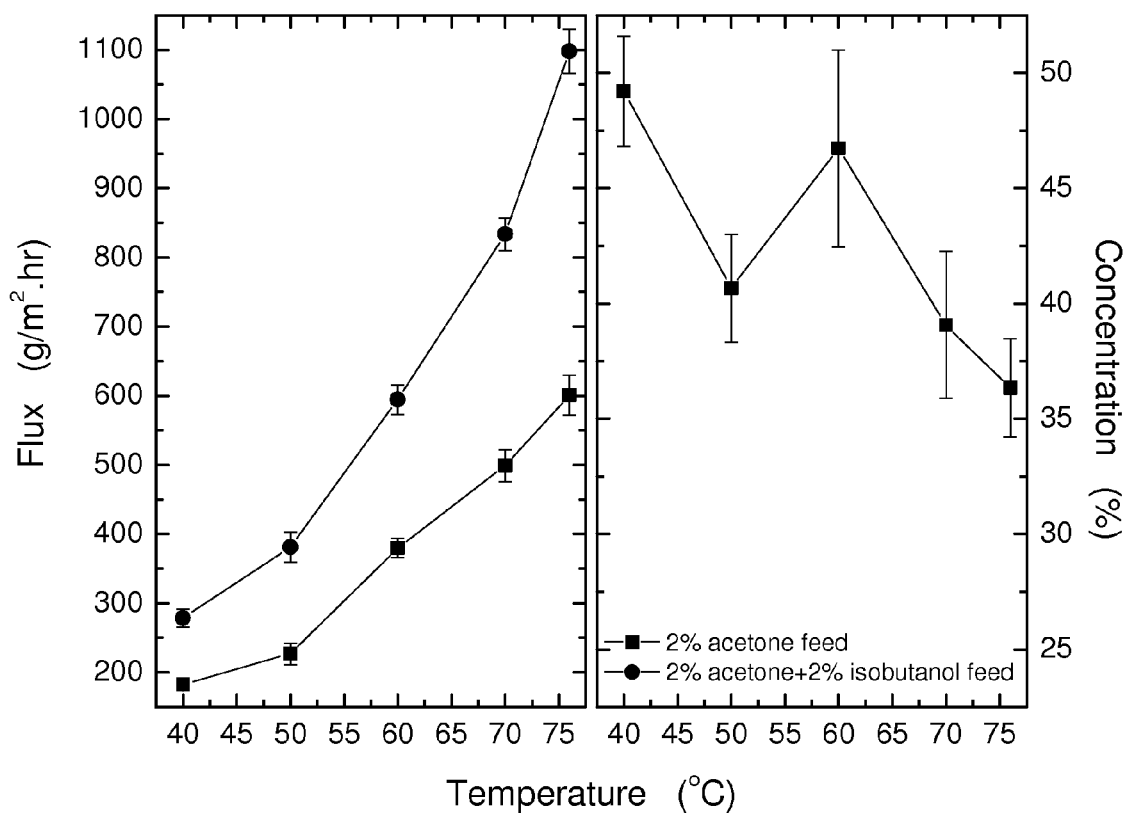

FIG. 21. Pervaporation results for 2% acetone (■) and 2% acetone+2% isobutanol mixture (•) (w/w) as a function of temperature for the SDS copolymer membrane with a molecular weight and PDMS volume fraction of 117 kg/mol and 0.83, respectively.

Figure 22:
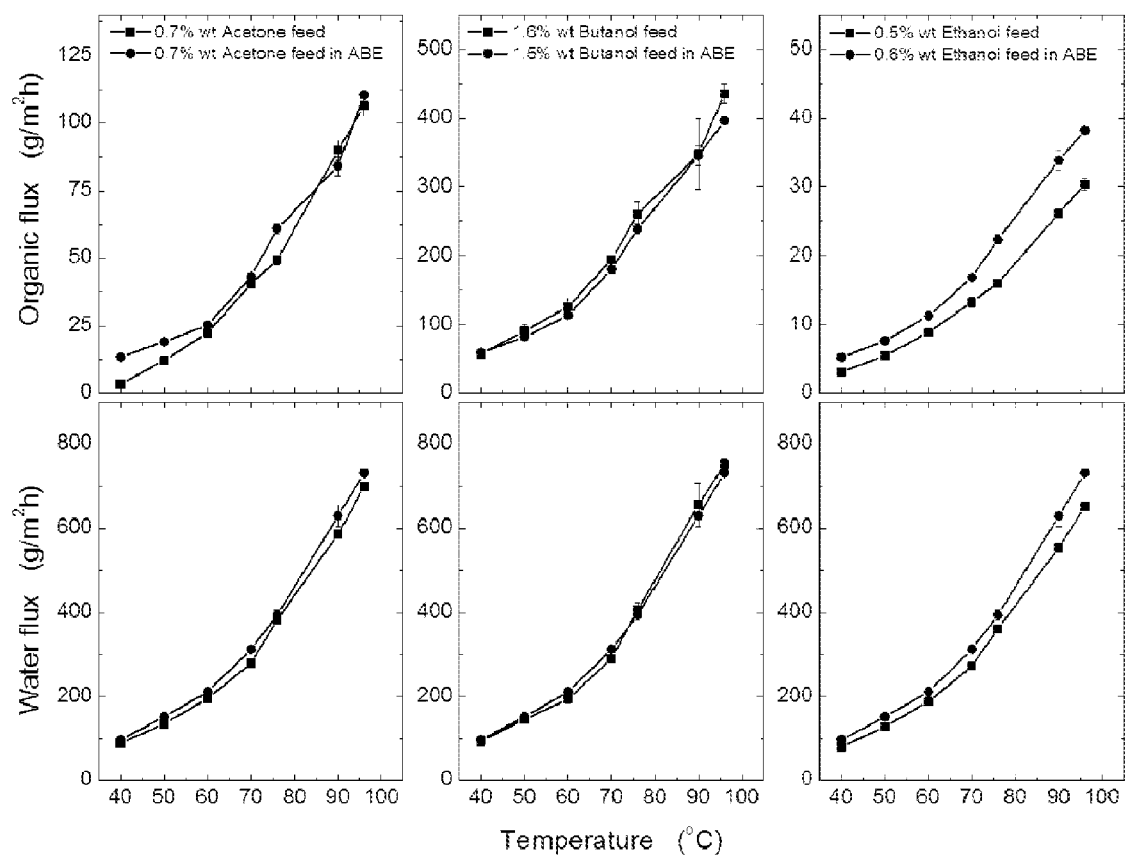

FIG. 22. Pervaporation experiments with binary mixtures of acetone-water, n-butanol-water and ethanol-water were performed to determine the separation efficiency of SDS membranes. The experiments were performed using ~0.7% wt acetone, ~1.5% wt n-butanol, and ~0.5% wt ethanol in deionized water at 40, 50, 60, 70, 76, 90 and 96° C. These compositions correspond to acetone, n-butanol and ethanol concentrations in *clostridium acetobutylicum* fermentation broth.

Figure 23:
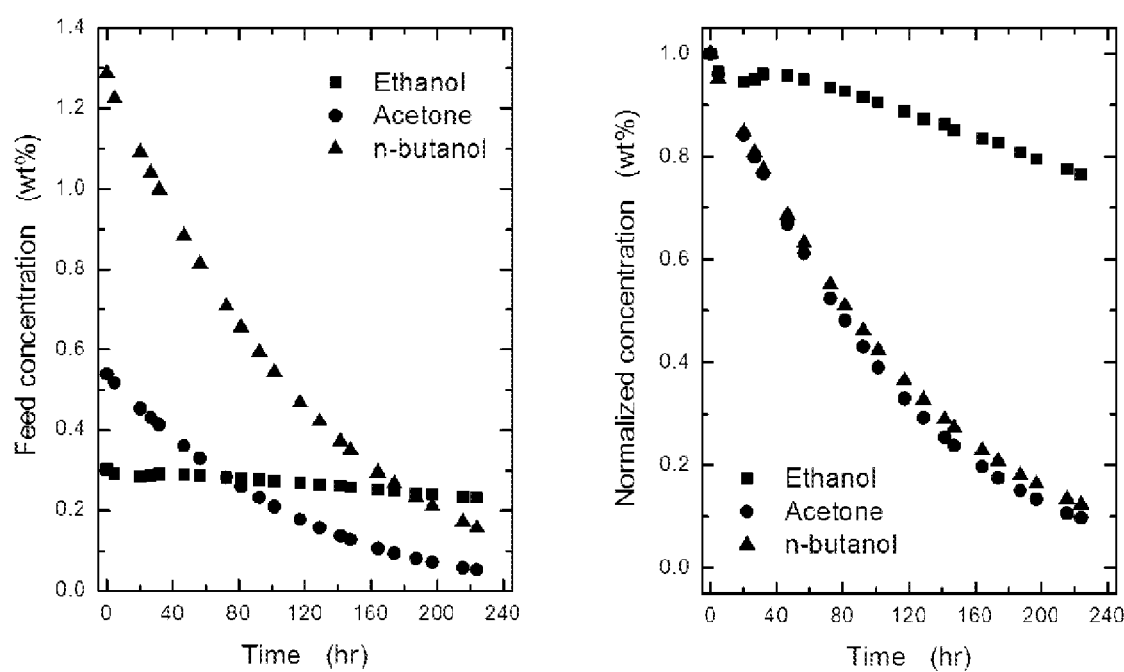

FIG. 23. Pervaporation experiment with ABE fermentation broth: feed concentration versus time.

Figure 24:
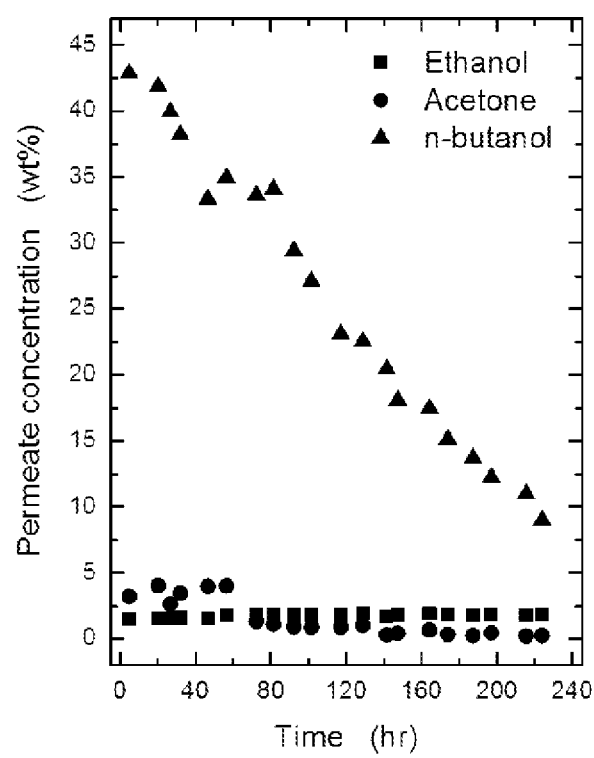

FIG. 24. Pervaporation experiment with ABE fermentation broth: permeate concentration versus time.

Figure 25:
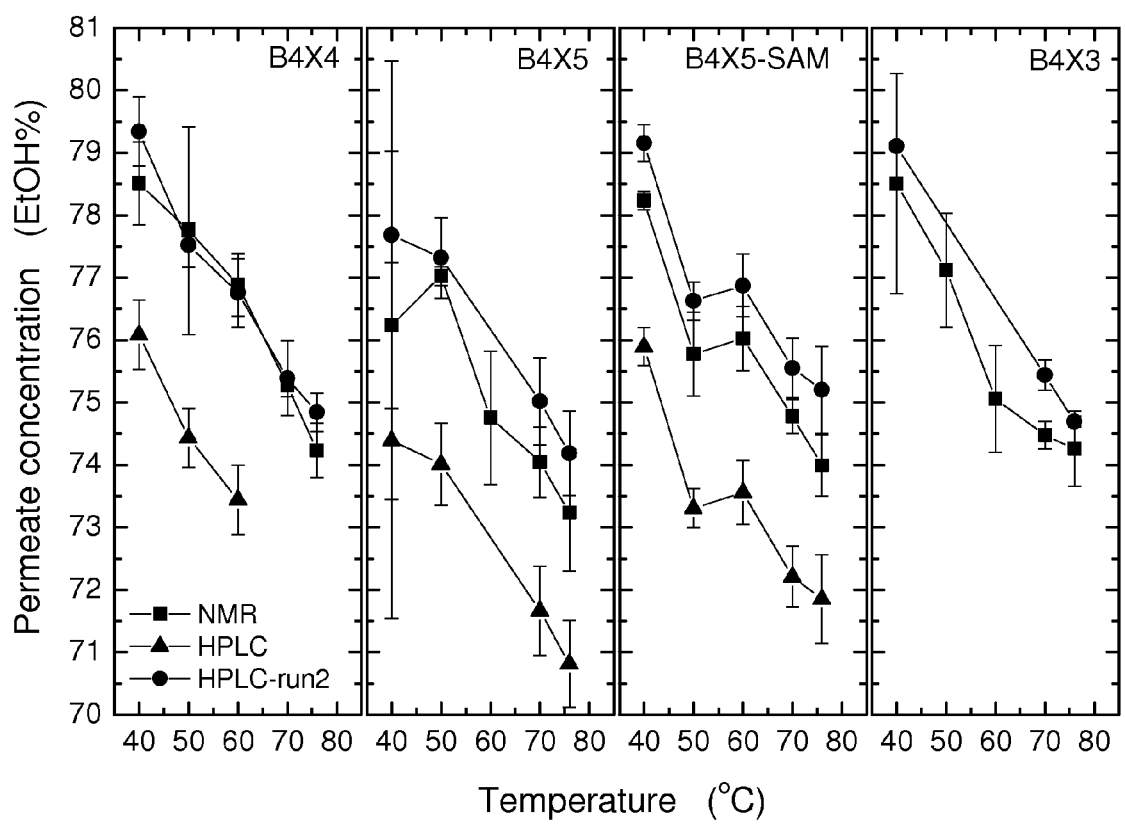

FIG. 25. Comparison of NMR and HPLC for determining ethanol concentration in the permeate for different SDS copolymer membranes.

Figure 26:
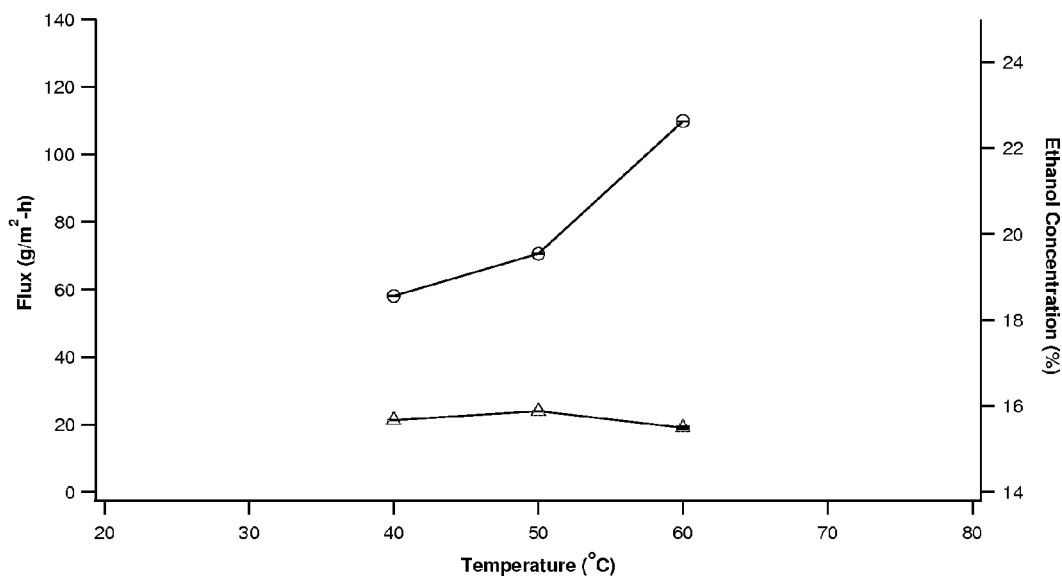
Figure 26:
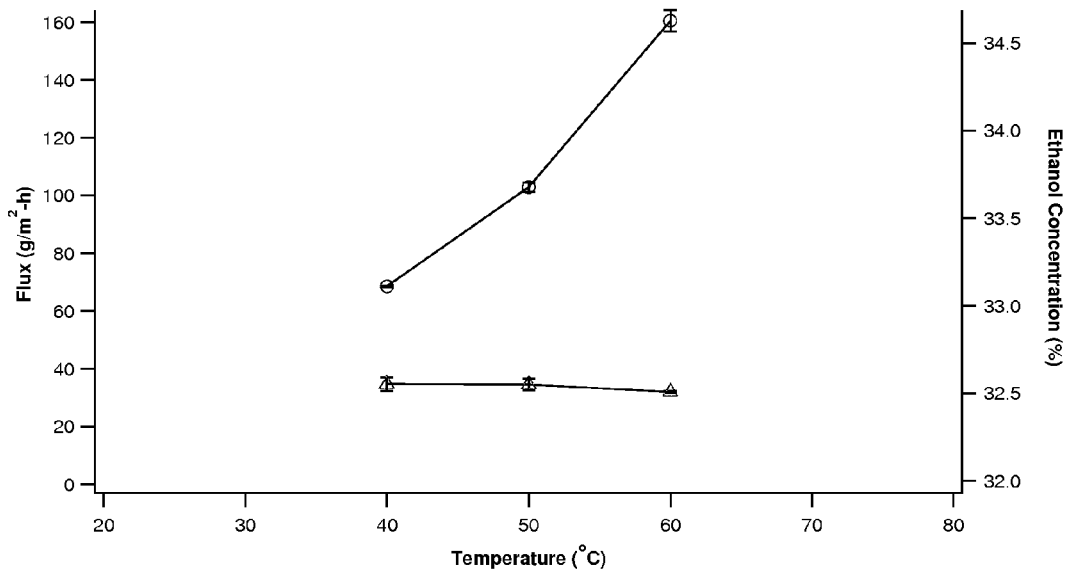

FIG. 26. Comparative ethanol separation data of (a) PS-g-PDMS graft copolymer membrane (SB105) and (b) PS-PDMS-PS triblock copolymer membrane (B3X4).

Figure 27:
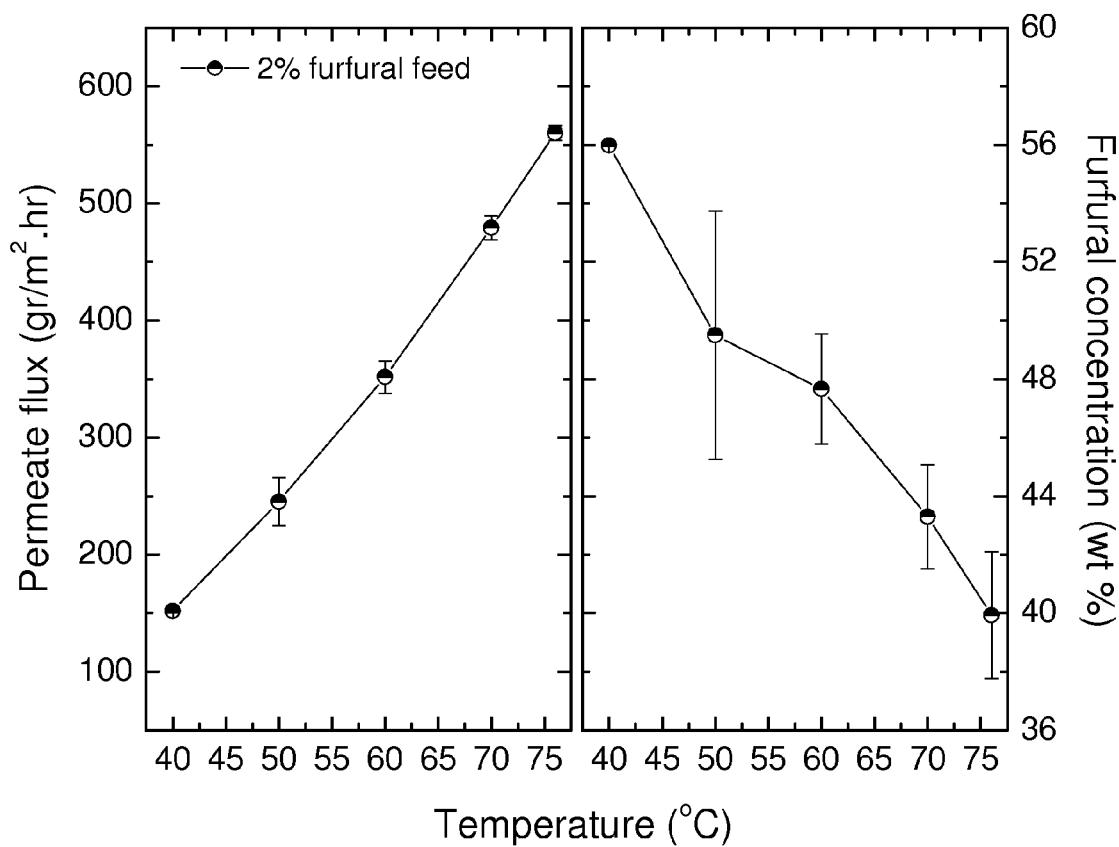

FIG. 27. Permeate flux and furfural concentration through a PS-PDMS-PS triblock copolymer membrane (B4X3).

Figure 28:
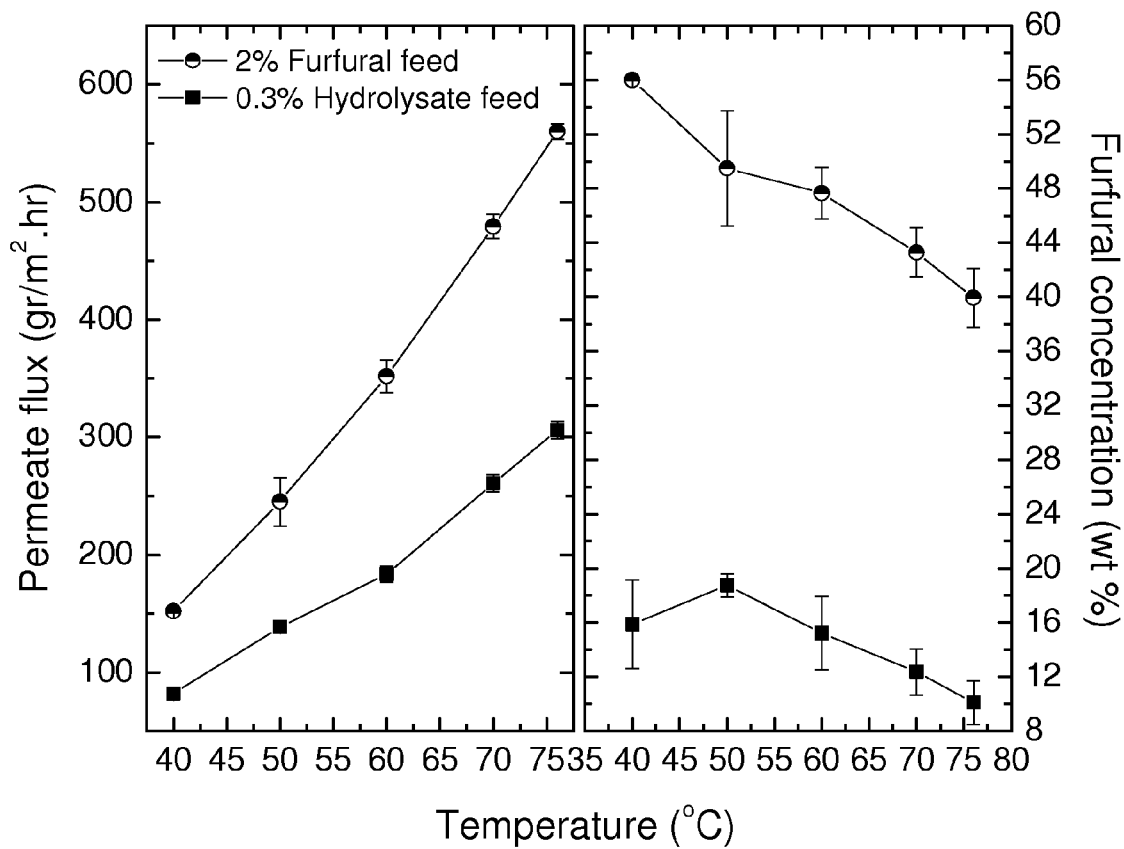

FIG. 28. Permeate flux and furfural concentration through a PS-PDMS-PS triblock copolymer membrane (B4X3) for 2% w/w furfural feed and a lignocellulosic hydrolysate feed containing furfural.

Figure 29:
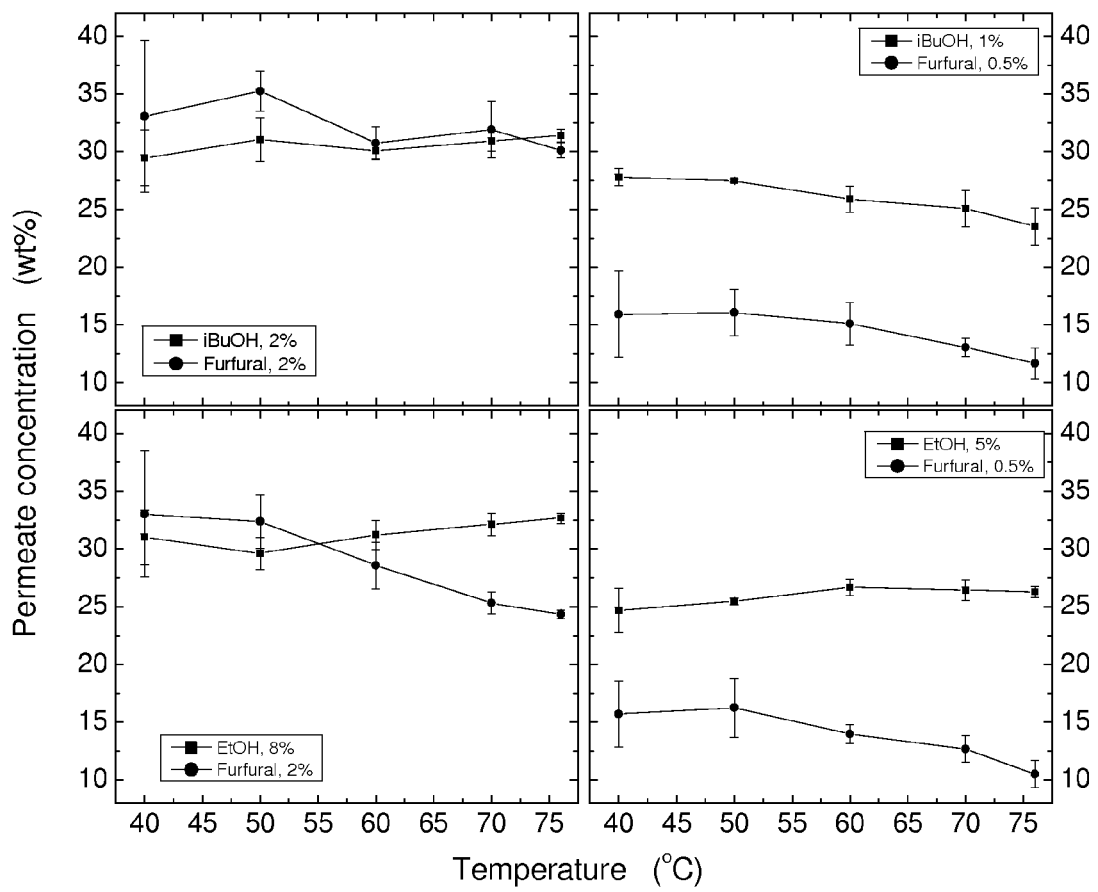

FIG. 29. Permeate concentrations for the mixed feeds of ethanol+furfural and isobutanol+furfural at different concentrations through a PS-PDMS-PS triblock copolymer membrane (B4X4).

Figure 30:
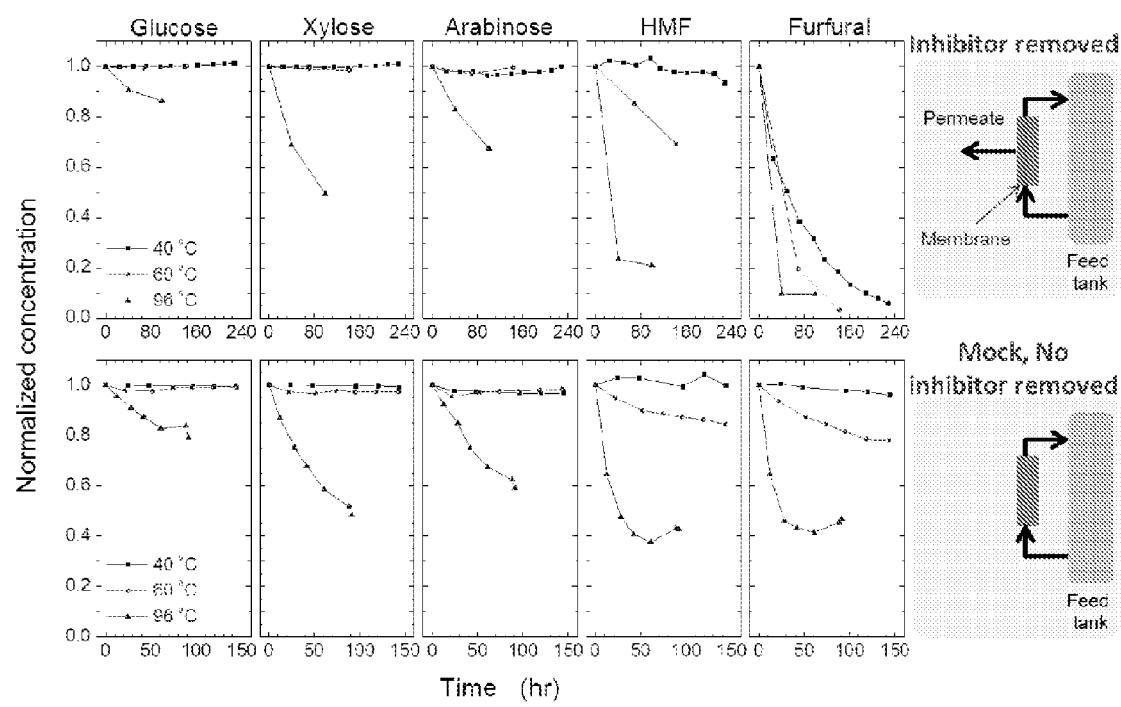

FIG. 30. Pervaporation experiments performed at 40, 60, and 96° C. to facilitate removal of toxins from pretreated biomass.

Figure 31:
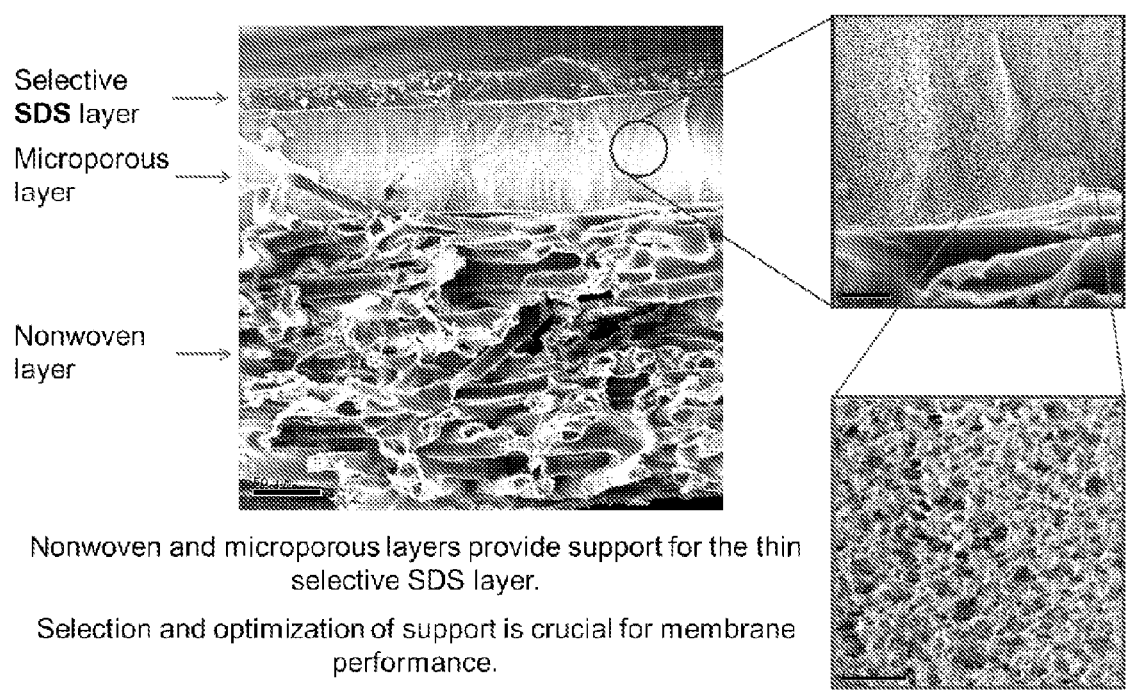

FIG. 31. SEM image of a thin SDS layer on a porous support (thin film composite membrane—TFC).

Figure 32:
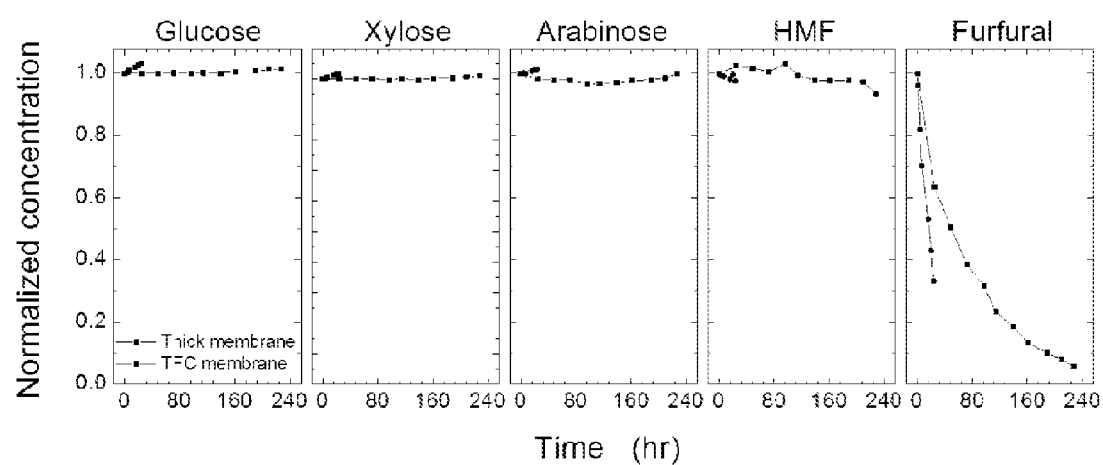

FIG. 32. Pervaporation performed with SDS-TFC membrane.

Figure 33:
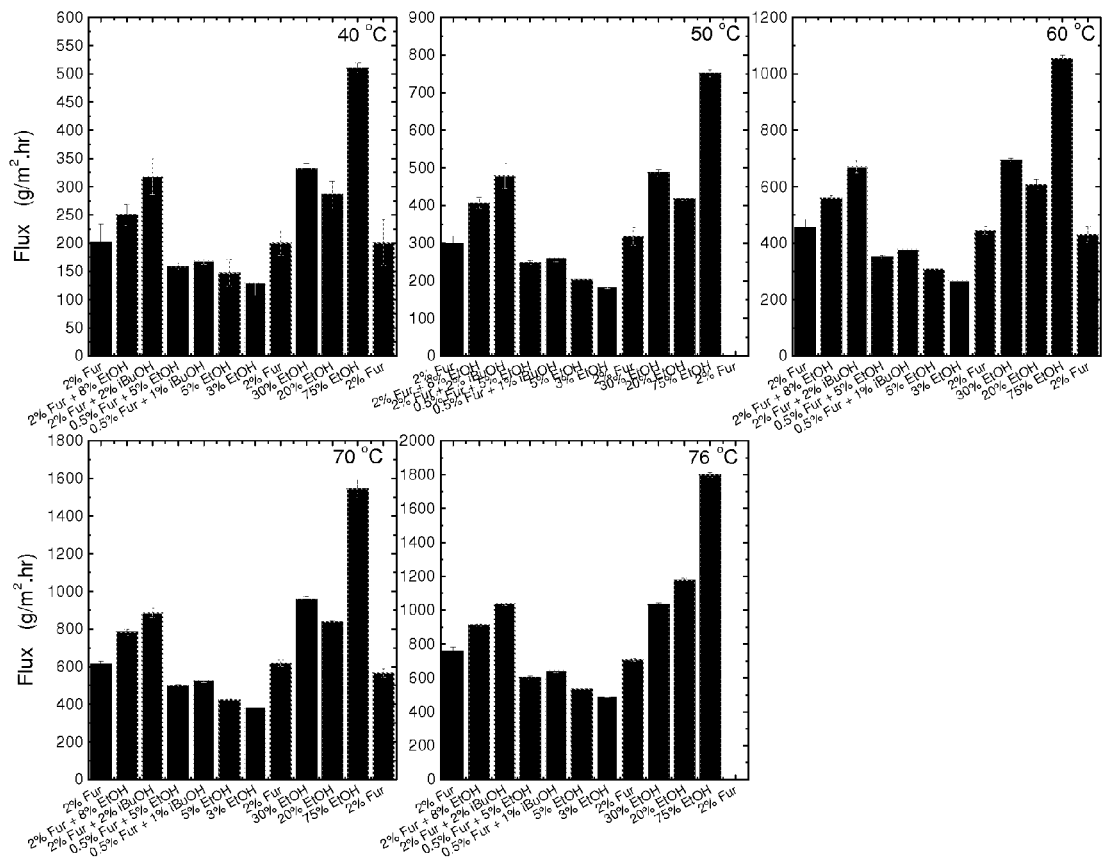

FIG. 33. Permeate flux values for different furfural and alcohol feed mixtures at 40, 50, 60, 70, and 76° C. through a PS-PDMS-PS triblock copolymer membrane (B4X4).

Figure 34:
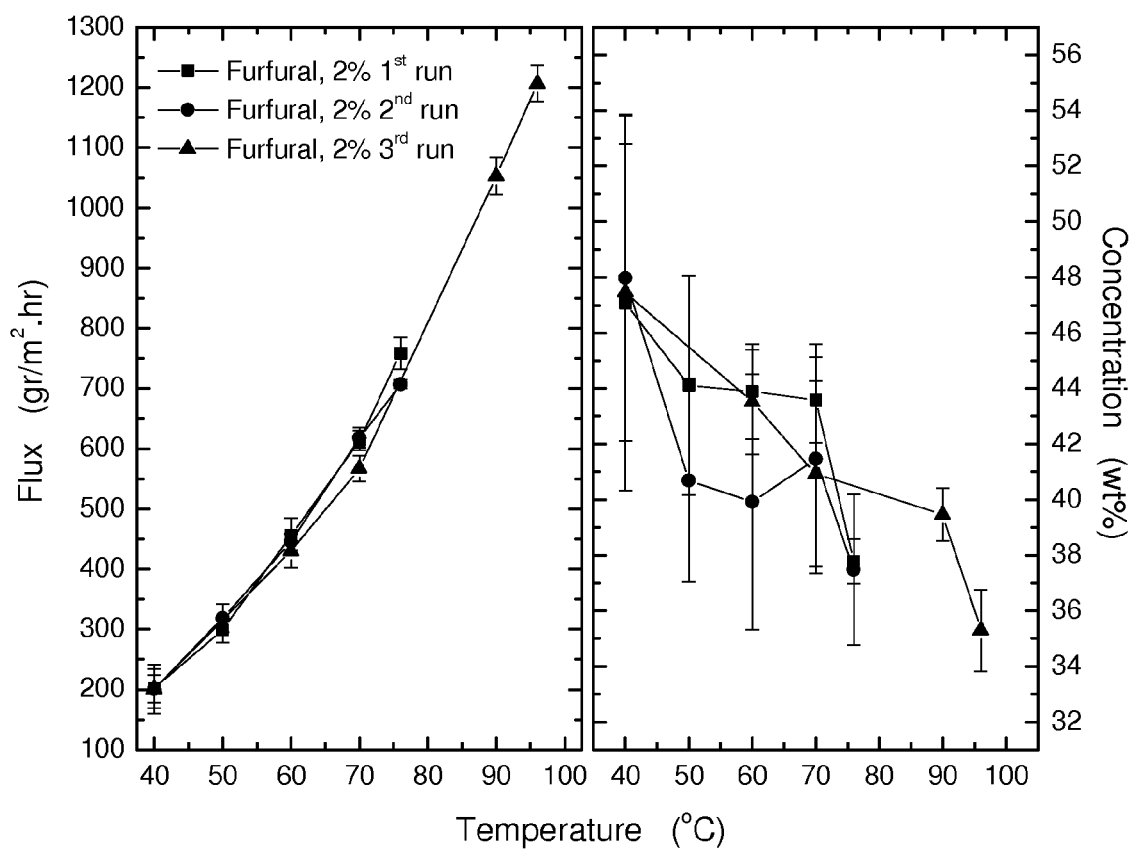

FIG. 34. Permeate flux and furfural concentration through a PS-PDMS-PS triblock copolymer membrane (B4X4) as a function of temperature.

DETAILED DESCRIPTION

The following description sets forth exemplary methods, parameters and the like. It should be recognized, however, that such description is not intended as a limitation on the scope of the present proposed invention but is instead provided as a description of exemplary embodiments.

1. Definitions

As used herein, the term "alkyl" includes straight-chain, branched-chain, and cyclic monovalent hydrocarbyl radicals, and combinations of these. Examples include methyl, ethyl, isobutyl, cyclohexyl, cyclopentylethyl, and the like.

As used herein, the term "block copolymer" includes polymers that include at least two blocks, where each block contains a different polymerized monomer type than the adjacent block or blocks. For example, a "diblock copolymer" may include a polymerized block of monomer A and an adjacent polymerized block of monomer B, represented as AB. A "triblock copolymer" may include two end blocks of polymerized monomer A flanking a middle block of polymerized monomer B, represented as ABA. Alternatively, a triblock copolymer may contain three different polymerized monomers represented as ABC. In preferred embodiments, the triblock copolymers disclosed herein are triblock copolymers with the blocks arranged in an ABA pattern. More specifically, in some preferred embodiments, the triblock copolymer is a poly(styrene-b-dimethylsiloxane-b-styrene) copolymer containing a polydimethylsiloxane middle block and polystyrene end blocks flanking the middle block as shown in FIG. 1.

As used herein, the term "lamellar morphology" includes a phase domain morphology having layers of alternating compositions that generally are oriented parallel with respect to one another. In some embodiments, the domain size is 15-100 nm. In some embodiments, the morphologies are bicontinuous. The term "lamellar morphology" also includes performated lamellae.

As used herein, the term "cylindrical morphology" includes a phase domain morphology having discrete tubular or cylindrical shapes. The tubular or cylindrical shapes may be hexagonally packed on a hexagonal lattice. In some embodiments, the domain size is 15-100 nm. In some embodiments, the morphologies are bicontinuous.

As used herein, the term "gyroid morphology" includes a phase domain morphology having a network structure with triply connected junctions. In some embodiments, the domain size is 15-100 nm. In some embodiments, the morphologies are bicontinuous.

As used herein, the term "double diamond morphology" includes a phase domain morphology having a double-diamond symmetry of space group Pn3m. In some embodiments, the domain size is 15-100 nm. In some embodiments, the morphologies are bicontinuous.

As used herein, the term "aqueous mixture" includes a mixture of components where at least one of the components is water. The "aqueous mixture" may be in the liquid or gas phase. In some embodiments, the aqueous mixture of interest is produced by a fermentation process.

As used herein, the terms "polystyrene-polydimethylsiloxane-polystyrene," "styrene-dimethylsiloxane-styrene," "poly(styrene-b-dimethylsiloxane-b-styrene)," "PS-b-PDMS-b-PS," "PS-PDMS-PS," and "SDS" may be used interchangeably and refer to triblock copolymers including three segments or sections: a polydimethylsiloxane middle block and polystyrene end blocks flanking the middle block.

As used herein, the term "optionally substituted" indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Typically, 0-4 such substituents are present, and in some substituted embodiments, 1-2 substituents are present. The substituents are independently selected from the group consisting of C1-C6 alkyl, aryl, OR, halo, $CO_2R$, $CONR_2$, and CN, where R=C1-C6 alkyl or H. Where an optional substituent is attached via a double bond, such as a carbonyl oxygen (=O), the group takes up two available valences, so the total number of substituents that may be included is reduced according to the number of available valences.

As used herein, the term "flux" refers to the mass per permeation area per time of individual permeants as they permeate through a membrane. Generally, flux depends on the thickness of the membrane, the feed composition, the temperature of the feed, the downstream vacuum, and the feed-side pressure. Throughout the disclosure, when flux data is presented, it is normalized to a membrane thickness of 50 micrometers. In particular embodiments, the feed composition includes the particular component of interest at a concentration of about 1% to 45% by weight of the solution. In particular embodiments, the feed composition includes the particular component of interest at a concentration of about 1% to 75% by weight of the solution. In particular embodiments, the temperature of the feed ranges from 40 to 76° C. within ±0.1° C. In particular embodiments, the downstream vacuum ranged from 2-4 mbar and the feed-side pressure was atmospheric pressure.

As used herein, the term "byproducts" refers to refers to byproducts and/or co-products formed during the process of converting a lignocellulosic feedstock into biofuels and/or other chemicals. The byproducts may be formed in any of the processing steps, for example pretreatment, hydrolysis or fermentation; and many of these may be toxic to the fermenting organism or to the enzymes used in an enzymatic hydrolysis. Some of the byproducts may, however, be not be toxic to the fermenting organism.

2. Description Of The Invention

The present disclosure relates to high molecular weight polystyrene-polydialkylsiloxane-polystyrene (hereafter "SDS") triblock copolymer compositions and methods of separating one or more organic compounds from an aqueous solution using membranes derived from SDS triblock copolymers. In some embodiments, the methods disclosed herein separate the one or more organic compounds from an aqueous solution produced in a fermentation process. In some embodiments, the one or more organic compounds include an alcohol, such as, for example, ethanol. In other embodiments, the one or more organic compounds include acetone. In other embodiments, the one or more organic compounds include acetone, ethanol, and n-butanol produced in an acetone-ethanol-n-butanol (ABE) fermentation process. In other embodiments, the one or more organic compounds include one or more byproducts produced in a fermentation process. In some embodiments, the one or more organic compounds that are suitable for such separation processes are hydrophobic so they are able to permeate through the membrane and have a boiling point in the range that is suitable for pervaporation.

In general, the SDS copolymer compositions are hydrophobic to hinder the permeation of water molecules. Additionally, the SDS copolymer compositions contain a structural block that imparts essential mechanical properties to the membrane (e.g., polystyrene) and may also contain an alcohol transporting block (e.g., polydimethylsiloxane).

A. Synthesis of SDS Triblock Copolymers

The PS-b-PDMS-b-PS (SDS) triblock copolymer may be synthesized via sequential anionic copolymerization route as shown in FIG. 1. High molecular weight SDS polymers may be unexpectedly produced given careful selection of the polymerization promoter and rigorous purification of the promoter, reagents, and solvents. Use of the polymerization promoter diglyme with highly purified reagents and solvents produced SDS polymers with molecular weights greater than 110 or 120 kg/mol and up to 1000 kg/mol. In some embodiments, high molecular weight copolymers form membranes with good mechanical properties to selectively separate one or more organic compounds from aqueous mixtures. However, in other embodiments, membranes containing SDS copolymers with molecular weights ranging from 40 kg/mol to 110 or 120 kg/mol have been prepared and have been used to selectively separate one or more organic compounds from aqueous mixtures. To synthesize high molecular weight SDS polymers, the first PS block was synthesized and then the PS block was end-capped with hexamethylcyclotrisiloxane monomer (as used herein, "D3" monomer) and subsequent polymerization of the PDMS block yielded PS-b-PDMS diblock copolymers. The polymerization of the PDMS block was achieved after the diglyme promoter that changes the polarity of the polymerization medium was added into the reactor (cf. FIG. 2). The extent of polymerization of D3 monomer was kept low (≈30-40% conversion) to attain better control over the molecular weight distribution of the copolymers as tabulated in Table 1. Finally, SDS triblock copolymers were obtained via coupling of PS-b-PDMS diblock copolymers with dichlorodimethylsilane as the coupling agent. The coupling ratio of the SDS copolymers was determined by calculating the areas under the peaks of diblock and triblock portions of the copolymer from the SEC chromatograms. The coupling ratio of the SDS triblock copolymers seems to be the lowest for the copolymer with the highest molecular weight, but it does not follow a clear trend. The SDS copolymers with a coupling ratio of lower than ≈40-50% resulted in membranes with poor mechanical properties, therefore only the copolymers with a coupling ratio greater than 50% are amenable as membrane materials for pervaporation experiments.

The morphology and the d spacings of the SDS triblock copolymers were determined by SAXS experiments. The SAXS profiles of the SDS films were isotropic indicating that the casting process led to randomly oriented grains. The SAXS profiles, d spacings, and morphologies of the SDS triblock copolymers were represented and tabulated in FIG. 3 and Table 1, respectively. In some embodiments, the morphology is cylindrical, lamellar, double diamond, or gyroid. In some preferred embodiments, the morphology is cylindrical or lamellar. In other preferred embodiments, the morphology is cylindrical. All of the profiles contain a primary peak at scattering vector, $q=q^*$. This enables determination of the domain spacing, $d=2\pi/q^*$, which changes from 28 to 79 nm. The d spacing of the SDS copolymers increase with increasing molecular weight for the given morphology except for the copolymer with a PDMS volume fraction (as used herein "$\phi_{DMS}$") and molecular weight of 0.82 and 131.3 kg/mol, respectively.

TABLE 1

Characteristics of the SDS copolymers synthesized for pervaporation experiments.

| Sample | $\phi_{PDMS}$ | Mol$_{PDMS}$ (%) | Wt$_{PDMS}$ (%) | $M_n$ (kg/mol) | PDI$_{diblock}$ | Coupling ratio (%) | d spacing (nm) | Morphology |
|---|---|---|---|---|---|---|---|---|
| B4X4 | 0.83 | 86 | 82 | 117.4 | 1.06 | 100 | 42.7 | Cylindrical |
| B4X5 | 0.82 | 86 | 81 | 131.3 | 1.06 | 100 | 36.2 | Cylindrical |
| B2X2 | 0.78 | 82 | 77 | 47.8 | 1.08 | 81.9 | 28.3 | Cylindrical |
| B3X2 | 0.73 | 78 | 71 | 150.0 | 1.03 | 70.3 | 53.3 | Cylindrical |
| B4X3 | 0.73 | 78 | 72 | 163.8 | 1.04 | 69.5 | 60.4 | Cylindrical |

TABLE 1-continued

Characteristics of the SDS copolymers synthesized for pervaporation experiments.

| Sample | $\phi_{PDMS}$ | Mol$_{PDMS}$ (%) | Wt$_{PDMS}$ (%) | $M_n$ (kg/mol) | PDI$_{diblock}$ | Coupling ratio (%) | d spacing (nm) | Morphology |
|---|---|---|---|---|---|---|---|---|
| B3X3 | 0.62 | 68 | 60 | 179.0 | 1.04 | 46.3 | 79.0 | Lamellar |
| B3X4 | 0.59 | 65 | 57 | 110.0 | 1.05 | 90.0 | 50.9 | Lamellar |

Thermo-oxidative degradation behavior of the copolymers was determined with thermo gravimetric analysis (hereinafter, "TGA") measurements in air. The temperature at which the polymer specimen reaches 95% of its original weight during the experiment is taken as a measure of stability and it is plotted as a function of PDMS volume fraction in FIG. 4. The standard PS sample lost 5% of its original weight at 175.6±3.3° C. and the stability of SDS samples increased with increasing PDMS volume fraction in a linear fashion and reached 356.8±23.1° C. Increased thermal stability of SDS copolymers compared to standard PS sample was expected due to stable nature of siloxanes at high temperatures.

Differential scanning calorimetry (hereinafter, "DSC") experiments were carried out to determine the glass transition temperatures of PDMS and PS blocks of SDS copolymers (FIG. 5). The glass transition temperature of PDMS blocks of SDS copolymers were measured in the range of −122.6° C. to −124.8° C., which is in close agreement with the glass transition temperature of PDMS network. However, the glass transition temperature of PS block of the copolymers with short PS blocks showed a deviation from the $T_g$ of standard PS sample, because the molecular weight of the PS blocks were lower than the entanglement molecular weight of PS. In addition, an endotherm peak for the cold crystallization of the PDMS block was observed around −45° C. for the SDS copolymer, which is characteristic behavior of PDMS samples. The area under the cold crystallization peak increases with increasing PDMS volume fraction for SDS copolymers.

B. Preparation of SDS Membranes

The SDS triblock copolymers described herein may be fabricated into membranes. The membranes are fabricated by melt pressing the copolymers between steel plates to obtain membranes having a thickness of about 10-200 μm.

It has been shown that the low surface tension of PDMS results in surface segregation of PDMS chains to air interface to lower the total free energy of the system. The wettability of SDS membranes was determined with water contact angle measurements on the both sides of the melt pressed membranes. The water contact angle of PS film was measured as 86±2.1° whereas the water contact angle of the SDS membranes were measured as ≈110° regardless of the PDMS volume fraction (FIG. 6). Without being bound by any theory, this behavior suggests that the surface segregation of PDMS block took place and the membranes became more hydrophobic. This is important for pervaporation experiments, because the surface of the membranes is covered by the alcohol-transporting PDMS phase. In addition, the wettability of the front and back sides of the SDS membranes were almost the same, because the membranes were prepared by melt pressing in between two PTFE sheets which resulted in similar driving force for the PDMS chains on both top and bottom side of the membranes for surface segregation.

C. Selective Alcohol Transport

The SDS triblock copolymers as described herein, may be used to fabricate membranes for the separation of an alcohol from an aqueous solution. The separation is carried out by contacting the membrane fabricated from any of the SDS triblock copolymers disclosed herein with an aqueous mixture containing at least one alcohol whereby the alcohol selectively permeates through the membrane to form a permeate containing the alcohol at a concentration greater than the concentration of the alcohol of the aqueous mixture. In some embodiments, the alcohol is a C2-C10 alcohol. In other embodiments, the alcohol is selected from the group consisting of ethanol, n-butanol, 2-butanol, isobutanol, 1-pentanol, 1-hexanol, 1-heptanol, 1-octanol, 1-nonanol, and 1-decanol. In some embodiments, the separation is carried out using pervaporation, a technique known in the art. Generally, in a pervaporation run, the aqueous mixture containing the alcohol is contacted on one side ("upstream side") of the membrane fabricated from SDS triblock copolymers at ambient pressure and a vacuum is applied on the other side ("downstream side") of the membrane. The alcohol then permeates from the upstream side of the membrane to the downstream side of the membrane to form a permeate enriched in alcohol relative to the feed aqueous mixture.

The SDS membranes may separate any concentration of the alcohol in an aqueous solution. In some embodiments, the aqueous mixture includes ethanol at a concentration of about 1-99% by weight of the aqueous mixture. In some preferred embodiments, the aqueous mixture includes ethanol at a concentration of about 3-75% by weight of the aqueous mixture. In some embodiments, after the separation, the permeate includes ethanol at a concentration of about 20-85% by weight of the permeate. In some embodiments, the aqueous mixture includes n-butanol at a concentration of about 0.5-8% by weight of the aqueous mixture. In some embodiments, after the separation, the permeate includes n-butanol at a concentration of about 30-85% by weight of the permeate. In some embodiments, the aqueous mixture includes isobutanol at a concentration of about 0.5-9.5% by weight of the aqueous mixture. In some embodiments, after the separation, the permeate includes isobutanol at a concentration of about 20-85% by weight of the permeate. In some embodiments, the aqueous mixture includes 2-butanol at a concentration of about 0.5-12.5% by weight of the aqueous mixture. In some embodiments, the aqueous mixture further includes acetone at a concentration of about 0.5-3% by weight of the aqueous mixture. In some embodiments, after the separation, the permeate includes acetone at a concentration of about 30-55% by weight of the permeate.

Generally, the membranes disclosed herein have a separation factor in the range of about 1.0 to 4.0 and fluxes that increase with increasing temperature and increasing PDMS volume fraction. For example, in some embodiments, the membrane has a flux in the range of about 50 to about 600 g/m$^2$-h at about 40° C. In other embodiments, the membrane has a flux in the range of about 100 to about 800 g/m$^2$-h at about 50° C. In other embodiments, the membrane has a flux in the range of about 175 to about 1100 g/m$^2$-h at about 60° C. In other embodiments, the membrane has a flux in the range of about 200 to about 1600 g/m$^2$-h at about 70° C. In other embodiments, the membrane has a flux in the range of about 300 to about 1800 g/m²-h at about 75° C. In some embodiments, the membranes disclosed herein have a separation factor in the range of about 1.0 to 4.0

In one exemplary embodiment, the concentration of ethanol is 8% by weight of the aqueous solution and was used as the feed. Results of the 8% (w/w) ethanol pervaporation experiments are summarized in FIG. 7. In this example, the permeate flux increases with increasing temperature and reached 374.2±8.0 g/m²·hr for the SDS membrane with PDMS volume fraction of 0.83 at 60° C. The ethanol concentration in the permeate reached ≈47% (w/w) for all the membranes with PDMS volume fractions above 0.62 regardless of the temperature of the feed. The permeate flux for 8% ethanol feed is plotted as a function of PDMS volume fraction for 40, 50, and 60° C. in FIG. 8. The permeate flux increased up to 0.73 PDMS volume fraction and then leveled off at 150, 250, and 360 g/m²·hr for 40, 50, and 60° C. feed temperatures. The membrane separation factor for 8% ethanol feed was calculated using equation 3, infra, and plotted as a function of temperature in FIG. 9 for SDS copolymers. The membrane separation factor for SDS membranes ranged from 2.2 to 2.6 for all the samples except the membrane with a PDMS volume fraction of 0.59 which ranged from 1.8 to 2.0.

In another exemplary embodiment, the ethanol feed composition was increased to 45% to simulate a second pervaporation run that would be carried out on the permeate of the 8% (w/w) ethanol run discussed above (FIG. 10). The pervaporation experiments were carried out at 40, 50, and 60° C. as well as 70 and 76° C. to see the effect of higher temperatures on flux and ethanol concentration. The permeate flux increased to ≈800 g/m²·hr and 1400 g/m²·hr at 60° C. and 76° C., respectively. The ethanol concentration in permeate was ≈74-78% at 40° C. for all the SDS membranes except the one with 0.59 PDMS volume fraction. The ethanol concentration decreased down to ≈73-75% at 76° C. with increasing feed temperature, but the minor decrease in permeate concentration resulted in almost a 4 fold increase in the flux values. The permeate flux as a function of PDMS volume fraction for 45% ethanol feed followed a similar trend with 8% ethanol feed (FIG. 11).

In another exemplary embodiment, the separation of isobutanol from dilute aqueous solutions via pervaporation through SDS membranes was studied for 1 and 2% (w/w) isobutanol in deionized water. The increase in the size of the alcohol molecule compared to water molecule results in a decrease in the diffusion coefficient, but the increase in hydrophobicity of the alcohol molecule increases the solubility of it in the membrane. The permeability is defined as the product of solubility and diffusion of a compound in the membrane according to solution-diffusion mechanism. Therefore, the permeate flux for 1% isobutanol feed is as high as flux values obtained for 8% ethanol feed (cf. FIG. 12). The isobutanol concentration in the permeate ranges from 31 to 34% for all the SDS membranes except the copolymer with 0.59 PDMS volume fraction. The flux values as a function of PDMS volume fraction followed the same trend as 8 and 45% ethanol feeds, increased with increasing PDMS volume fraction up to 0.73 and then leveled off as shown in FIG. 13.

The increase in isobutanol feed concentration lead to an increase in both flux and isobutanol concentration in permeates as shown in FIG. 14. The flux values increased ≈30% due to the increase in the feed concentration and reached ≈450 g/m²·hr and 800 g/m²·hr at 60 and 76° C., respectively. The flux is plotted as a function of PDMS volume fraction in FIG. 15 for the all the feed temperatures studied, the flux increased up to PDMS volume fraction of 0.73 and then leveled off. The isobutanol concentration by weight of the permeate was measured and ranged from 46 to 52% except for the SDS membrane with PDMS volume fraction of 0.59. The higher fluctuation in the permeate concentration is because of the dilute feed concentration and high flux of the permeate. The effect of isobutanol concentration on the permeate concentration is represented in Table 2. The feed concentration decreases as the pervaporation experiment takes place and the decrease in the feed concentration resulted in a decrease in the permeate concentration.

TABLE 2

Dependence of permeate concentration on feed composition for isobutanol.

| Temperature (° C.) | Feed concentration (wt %) | Permeate Concentration (wt %) | St Dev |
| --- | --- | --- | --- |
| 75 | 1.94 | 47.43 | 0.73 |
| 70 | 1.89 | 47.86 | 1.20 |
| 60 | 1.84 | 46.90 | 1.39 |
| 40 | 1.69 | 46.48 | 1.82 |
| 50 | 1.60 | 45.81 | 1.11 |

The solubility of isobutanol in water is 9.5% (w/w) and therefore the permeate through SDS membranes has 2 phases as shown on the left hand side of FIG. 16. The top phase of the permeate is isobutanol-rich and its composition was measured as 83% with NMR. The isobutanol-rich phase constitutes ≈60% of the total volume of the permeate and this phase can be purified further by a water-selective membrane to be blended with gasoline. The bottom phase of the permeate is water-rich and its composition is ≈8%, which can be refluxed back to feed or to another pervaporation unit for further enrichment. The low solubility of isobutanol in water allowed refinement of 2% feed to 83% permeate in single step pervaporation with high flux and selectivity.

In another exemplary embodiment, pervaporation of 1% (w/w) n-butanol feed was performed and the flux and n-butanol concentration are plotted as a function of temperature in FIG. 17. The flux values obtained for n-butanol are slightly greater than the flux values of isobutanol for the same feed concentration (1% w/w). Without being bound by any theory, this could be due to the molecular size of the molecules that affects the diffusion rates of the alcohols in the SDS membrane. The permeate concentration values are comparable for both isobutanol and n-butanol feeds with the same concentration. The n-butanol permeates also show 2 phases because of its low solubility in water (7.7% w/w), but the concentrations of the n-butanol-rich and water-rich phases were not analyzed. The flux values increased with increasing PDMS volume fraction as shown in FIG. 18 as opposed to flux values obtained for ethanol and isobutanol feeds.

In another exemplary embodiment, pervaporation of different ethanol feed compositions was performed and the flux as a function of temperature is plotted for different ethanol feed compositions (B4X4 membrane, 0.83 PDMS volume fraction) in FIG. 19. Flux increases with increasing temperature and it follows Arrhenius behavior. Ethanol concentration in permeate increases with increasing ethanol feed composition, but it does not change significantly with increasing temperature.

In another exemplary embodiment, the flux values showed Arrhenius behavior as a function of temperature and activation energies were calculated for the feeds at which pervaporation experiments were carried out at 5 different temperatures. The activation energies for 1 and 2% isobutanol feeds and 45% ethanol feed were plotted as a function of PDMS volume fraction in FIG. 20. The activation energies did not show any dependence on either PDMS volume fraction or feed composition. Without being bound by any theory, this may be due to high permeability and selectivity of PDMS block to alcohol compared to PS block of SDS copolymer membranes.

D. Selective Acetone Transport

Acetone is present in isobutanol fermentation processes. In another exemplary embodiment, an SDS copolymer membrane with a molecular weight and PDMS volume fraction of 117 kg/mol and 0.83, respectively, may be used to separate acetone from an aqueous mixture containing acetone at a concentration of 2% by weight of the aqueous mixture. In another exemplary embodiment, an SDS copolymer membrane with a molecular weight and PDMS volume fraction of 117 kg/mol and 0.83, respectively, may be used to separate acetone and isobutanol from an aqueous mixture containing acetone at a concentration of 2% acetone by weight and 2% isobutanol by weight of the aqueous mixture. The acetone flux reached 380 and 600 g/m$^2$·hr for 60 and 76° C., respectively, but the permeate concentration decreased with increasing temperature from 49% to 36% (w/w) for 40 and 76° C., respectively (cf. FIG. 21). The decrease in the permeate concentration may be due to 1) decreased selectivity and 2) depletion effect of acetone towards the end of the pervaporation experiment. For instance, the depletion effect may be observed in the 50° C. runs, as these runs were the last runs of the pervaporation experiment. The 50° C. run showed a lower concentration than expected. The addition of 2% isobutanol showed synergistic behavior and resulted in an increase in overall flux.

In another exemplary embodiment, pervaporation with binary mixtures of acetone-water, n-butanol-water and ethanol-water may be performed with SDS membranes as shown in FIG. 22. In some exemplary embodiments, the binary mixtures include ~0.7% wt acetone, ~1.5% wt n-butanol, and ~0.5% wt ethanol in deionized water at 40, 50, 60, 70, 76, 90, and 96° C. These binary mixtures correspond to acetone, n-butanol and ethanol concentrations in *clostridium acetobutylicum* fermentation broth. In another exemplary embodiment, pervaporation with an acetone, n-butanol, ethanol and water quarternary mixture (ABE mixture) may be performed.

In another exemplary embodiment, pervaporation with an ABE fermentation broth may be performed as shown in FIG. 23 and FIG. 24. Generally, n-butanol and acetone concentration in the feed decreases much faster compared to ethanol concentration, since the SDS copolymer membrane is more selective to n-butanol and acetone compared to ethanol. The n-butanol concentration in the permeate was ~43% wt at the beginning of the pervaporation experiment, but it decreased with increasing time due to concentration depletion in the feed (see FIG. 23). The permeate was phase separated even the presence of ethanol and acetone in the permeate.

The concentration of the permeates from the pervaporation experiments were determined via NMR analysis using d$_6$-acetone as the NMR solvent. High performance liquid chromatography (HPLC) experiments were performed to double check the concentration values obtained with NMR for a series of pervaporation experiments carried out with 45% ethanol feed. The initial data obtained with HPLC showed some discrepancy with the NMR data as shown in FIG. 25. However, the modified calibration procedure for HPLC led to a better agreement between two different techniques of characterization.

E. Separation of Organic Compounds from Acetone-n-Butanol-Ethanol ("ABE") Fermentation Mixtures The SDS triblock copolymers described herein may also be used to fabricate membranes to selectively separate one or more organic compounds from an acetone-n-butanol-ethanol ("ABE") fermentation mixture. ABE fermentations are known in the art and are bacterial fermentation processes used to produce acetone, n-butanol, and ethanol from starch. In some embodiments, the one or more organic compounds include acetone, n-butanol, ethanol, or any mixture or combination thereof. In some embodiments, the separation is carried out using pervaporation techniques known in the art and described herein.

F. Comparative Experiments of SDS Triblock Copolymers and Polystyrene-Polydimethlsiloxane ("PS-g-PDMS") Graft Copolymers Polystyrene-polydimethlsiloxane ("PS-g-PDMS") graft copolymers were prepared as reported in *J. of Membrane Science*, v75, pp 93-105 (1992). The copolymers were synthesized by radical polymerization of styrene and dimethylsiloxane macromonomer using 2,2-azobisisobutyronitrile (AIBN) as the initiator. Characterization data of graft copolymer samples SB 102, SB 103, SB 104, and SB 105 are compared with the SDS triblock copolymer sample B3X4 in Table 3.

TABLE 3

Polymer characterization data of PS-g-PDMS graft copolymers and PS-PDMS-PS triblock copolymers

| Sample | M$_n$ kg/mol | PDI | φ$_{PDMS}$ | Mol$_{PDMS}$ (%) | Wt$_{PDMS}$ (%) |
|---|---|---|---|---|---|
| SB102 | 76 | 1.7 | 0.59 | 12 | 57 |
| SB103 | 70 | 2.0 | 0.70 | 19 | 68 |
| SB104 | 50 | 2.4 | 0.61 | 13 | 59 |
| SB105 | 149 | 2.5 | 0.36 | 5 | 34 |
| B3X4 | 100 | 1.12 | 0.59 | 65 | 57 |

A membrane could not be fabricated from the low molecular weight graft copolymer sample SB 103 (M$_n$=70 kg/mol) because the copolymer was too soft. A membrane fabricated from SB 104 (M$_n$=50 kg/mol) ruptured during pervaporation experiments at 50° C. and 60° C. In contrast, membranes were successfully fabricated from lower molecular weight PS-PDMS-PS triblock copolymers (e.g., molecular weight of 48 kg/mol) due to the better mechanical properties of the PS-PDMS-PS triblock copolymers. Thus, the PS-PDMS-PS triblock copolymers provide better mechanical properties over the PS-g-PDMS graft copolymers across a larger molecular weight range. A PS-g-PDMS membrane viable for pervaporation was fabricated from the higher molecular weight sample, SB105. FIG. 26 shows comparative ethanol separation data of (a) PS-g-PDMS graft copolymer membrane (SB105) and (b) PS-PDMS-PS triblock copolymer membrane (B3X4) under similar conditions. The PS-PDMS-PS triblock copolymer shows higher flux, membrane separation factor, and ethanol permeate concentration over the PS-g-PDMS graft copolymer.

G. Selective Transport of Byproducts Produced in Fermentation Processes

The SDS triblock copolymers described herein may also be used to fabricate membranes to selectively separate one or more byproducts produced in fermentation processes. The separation is carried out using pervaporation techniques known in the art and described herein. In some embodiments, the one or more byproducts compounds include acetic acid, formic acid, levulinic acid, succinic acid, furfural, 5-hydroxymethylfurfural, 2-furoic acid, vanillic acid, ferulic acid, p-coumaric acid, syringic acid (4-hydroxy-3,5-dimethoxybenzoic acid), 4-hydroxybenzoic acid; protocatechuic acid (3,4-dihydroxybenzoic acid); homovanillic acid (2-(4-hydroxy-3-methoxy-phenyl)acetic acid); caffeic acid (3,4-dihydroxycinnamic acid); sinapic acid; propionic acid; vanillylmandelic acid; 4-hydroxymandelic acid; 4-hydroxyphenylacetic acid; 3-hydroxybenzoic acid; 2,5-dihydroxybenzoic acid; benzoic acid; vanillin; syringaldehyde; 4-hydroxybenzaldehyde; coniferyl aldehyde (4-OH-3-OCH$_3$-cinnamaldehyde); sinapinaldehyde (3,5-dimethoxy-4-hydroxycinnamaldehyde); protocatechualdehyde (3,4-dihydroxybenzaldehyde); acetovanillone (4'-hydroxy-3'-methoxyacetophenone); acetosyringone (3',5'-dimethoxy-4'-hydroxyacetophenone); guaiacol; coniferyl alcohol (4-(3-hydroxy-1-propenyl)-2-methoxyphenol); hydroquinone; catechol (pyrocatechol); vanillyl alcohol (4-hydroxy-3-methoxybenzyl alcohol); eugenol; or any mixture or combination thereof. In some preferred embodiments, the one or more organic compounds include acetic acid, formic acid, levulinic acid, succinic acid, furfural, 5-hydroxymethylfurfural, or any mixture or combination thereof. In some embodiments, the one or more organic compounds is 5-hydroxymethylfurfural. In some embodiments, the one or more organic compounds include furfural.

In an exemplary embodiment, a solution of furfural in deionized water was prepared at a concentration of 2% w/w and the pervaporation experiments were performed at 40, 50, 60, 70, and 76° C. by using the membrane produced from the copolymer B4X3. The furfural concentration in the permeate decreased from 56 to 40% w/w with increasing temperature as shown in FIG. 27. The decrease in the permeate concentration is due to decreasing membrane selectivity and concentration depletion effect on the furfural feed.

In another exemplary embodiment, pervaporation experiments were performed on a lignocellulosic hydrolysate. The flux and furfural concentrations as a function of temperature with the membrane prepared from a SDS copolymer (B4X3) are shown in FIG. 28. The permeate flux is lower for the hydrolysate because the concentration of furfural in the hydrolysate feed was much lower than 2% w/w. The furfural concentration in the permeate decreases as with increasing temperature due to both loss of selectivity with increasing feed temperature and furfural concentration depletion effect.

In another exemplary embodiment, feed mixtures composed of a) isobutanol and furfural and b) ethanol and furfural were prepared at different concentrations to determine the effect of feed composition on the pervaporation performance using the membrane prepared with a SDS copolymer (B4X4). The concentrations of permeating species are shown in FIG. 29. The decrease in the permeate concentration with increasing feed temperature is due to loss of selectivity with increasing temperature and concentration depletion effect.

In another exemplary embodiment, pervaporation experiments may be performed at 40, 60, and 96° C. to facilitate removal of toxins from pretreated biomass as shown in FIG. 30. High temperature operation would allow higher flux values and removal of low vapor pressure toxins from pretreated biomass. However, high temperature and long experimental time resulted in degradation of sugars in pretreated biomass. Thin film composite membrane (TFC) or large membrane area is required for high temperature detoxification experiments. Moderate and low temperature (40 and 60° C.) operation resulted in removal of furfural from pretreated biomass.

In another exemplary embodiment, pervaporation experiments may be performed with thin film composite membranes with SDS copolymer as shown in FIG. 31. Such composite membranes may increase flux. To prepare composite membranes, the SDS copolymer may be dissolved in a solvent (like toluene, THF, cyclohexane, benzene, etc) at different compositions and the polymer solution is applied to a porous support membrane (like spraying, dip coating, brushing, etc.). The porous support may be reverse osmosis, nanofiltration or ultrafiltration membranes and can be prepared from polysulfone, polyacrylonitrile, or polyvinylidene fluoride. A thin selective SDS layer forms on the porous support as the solvent evaporates. An SEM image of the thin SDS layer and porous support is shown in FIG. 31. In some exemplary embodiments, SDS-TFC membranes may accelerate the detoxification process due to higher fluxes obtained with such membranes. Normalized furfural concentration in pretreated biomass decreased faster compared to thick SDS membranes as shown in FIG. 32.

In another exemplary embodiment, the stability of SDS copolymer membranes were tested in the pervaporation set-up for over ~10 days of continuous operation using different feeds at 40, 50, 60, 70 and 76° C. as shown in FIG. 33. The feeds were changed without removing the membrane from the pervaporation cell. The pervaporation run included feeds in the following order: 1) 2% w/w furfural, 2) 2% w/w furfural and 8% w/w ethanol, 3) 2% w/w furfural and 2% w/w isobutanol, 4) 0.5% w/w furfural and 5% w/w ethanol, 5) 0.5% w/w furfural and 1% w/w isobutanol, 6) 5% w/w ethanol, 7) 3% w/w ethanol, and 8) 2% w/w furfural. The second pervaporation run using a 2% w/w furfural feed was performed at the end of ~10 days to compare the concentration and flux data obtained in the first and last furfural pervaporation experiments, (labeled "1$^{st}$ run" and "2$^{nd}$ run" in FIG. 34). The comparison of the flux and permeate concentration values for the first and second runs of 2% w/w furfural feed (FIG. 34) demonstrates that the PS-PDMS-PS triblock copolymer membrane (B4X4) selectively permeates even after prolonged pervaporation experiments with different feed mixtures. The stability and performance was investigated in a third run of a 2% w/w furfural feed at 40, 50, 60, 70, 76, 90, and 96° C. (FIG. 34). The flux reached ~1300 g/m$^2$·hr at 96° C., but the furfural concentration in the permeate decreased to ~35% w/w. Decreasing the temperature to 90° C. resulted in a decrease in the flux values, but the furfural concentration in the permeate was increased to ~40% w/w. The flux and concentration values obtained for the first, second, and third furfural runs are in agreement, demonstrating that the performance of a PS-PDMS-PS triblock copolymer membrane (B4X4) did not deteriorate with time at high temperatures (FIG. 34).

H. Gas Permeation and Sorption of SDS Membranes

Gas permeation experiments were carried out to determine the oxygen ($O_2$) and carbon dioxide ($CO_2$) permeability through SDS triblock copolymer membranes. The $O_2$ and $CO_2$ permeabilities of the SDS copolymer membranes were plotted with flux and membrane separation factors for the pervaporation experiments carried out with 8% ethanol feed at 40° C. in Tables. 4 ($O_2$) and 5 ($CO_2$). The agreement between gas permeation and pervaporation data suggests that the reported gas permeation behavior of polymers can be utilized to select and design new copolymers for pervaporation membranes for alcohol transport.

TABLE 4

Oxygen permeability (at room temperature) and flux for 8% (w/w) ethanol feed (at 40° C.) for SDS copolymer studied.

| Sample | Oxygen permeability (Barrer) | St Dev | Total flux at 40° C. (gr/m²hr) | St Dev | Membrane separation factor at 40° C. | St Dev |
|---|---|---|---|---|---|---|
| B2X2 | 653.49 | 108.30 | 165.13 | 2.15 | 2.22 | 0.31 |
| B3X2 | 573.21 | 9.11 | 157.20 | 8.34 | 2.27 | 0.16 |
| B3X4 | 413.44 | 29.86 | 85.58 | 12.01 | 1.81 | 0.07 |
| B4X3 | 463.52 | 52.72 | 138.19 | 5.92 | 2.26 | 0.03 |
| B4X4 | 580.75 | 99.85 | 166.94 | 10.18 | 2.16 | 0.12 |
| B4X5 | 695.01 | 21.83 | 164.77 | 3.94 | 2.25 | 0.08 |

TABLE 5

Carbon dioxide permeability (at room temperature) and separation factor for 8% (w/w) ethanol feed (at 40° C.) for SDS copolymer studied.

| Sample | $CO_2$ permeability (Barrer) | St Dev | Total flux at 40° C. (gr/m²hr) | St Dev | Membrane separation factor at 40° C. | St Dev |
|---|---|---|---|---|---|---|
| B2X2 | 2944.77 | 153.26 | 165.13 | 2.15 | 2.22 | 0.31 |
| B3X2 | 2192.01 | 183.54 | 157.20 | 8.34 | 2.27 | 0.16 |
| B3X4 | 1585.03 | 173.98 | 85.58 | 12.01 | 1.81 | 0.07 |
| B4X3 | 2227.90 | 123.21 | 138.19 | 5.92 | 2.26 | 0.03 |
| B4X4 | 2777.37 | 231.68 | 166.94 | 10.18 | 2.16 | 0.12 |
| B4X5 | 2724.56 | 71.34 | 164.77 | 3.94 | 2.25 | 0.08 |

Sorption experiments with aqueous ethanol and isobutanol solutions were carried out to determine the swelling of the SDS membranes. The absorption of dilute ethanol and isobutanol in the SDS membranes was negligible and the data did not follow a trend as shown in Table 6. However, the stability of SDS membranes in pure isobutanol deteriorated at high temperatures, where the SDS membranes lost their structural integrity. The membranes with PDMS volume fractions above 0.82, 0.73, and 0.59 lost their integrity at 60° C., 70° C. and 76° C., respectively.

TABLE 6

Sorption experiments with aqueous solutions and pure alcohol.

1% isobutanol sorption

| Sample | $\phi_{PDMS}$ | $M_n$ (kg/mol) | 40° C. | 50° C. | 60° C. | 70° C. | 76° C. |
|---|---|---|---|---|---|---|---|
| B4X4 | 0.83 | 117.4 | 0.70 | 0.33 | 0.33 | 0.37 | 0.17 |
| B4X5 | 0.82 | 131.3 | 0.22 | 0.29 | 0.17 | 0.10 | 0.25 |
| B4X3 | 0.73 | 163.8 | 0.51 | 0.04 | −0.06 | 0.04 | 0.16 |
| B3X2 | 0.73 | 150.0 | 0.19 | 0.04 | −0.02 | 0.11 | 0.00 |
| B3X4 | 0.59 | 110.0 | 0.76 | 0.23 | 0.31 | 0.15 | 0.27 |

2% isobutanol sorption

| Sample | $\phi_{PDMS}$ | $M_n$ (kg/mol) | 40° C. | 50° C. | 60° C. | 70° C. | 76° C. |
|---|---|---|---|---|---|---|---|
| B4X4 | 0.83 | 117.4 | 0.67 | 0.29 | 0.58 | 0.20 | 0.21 |
| B4X5 | 0.82 | 131.3 | 0.67 | 0.83 | 0.29 | 0.61 | 0.37 |
| B4X3 | 0.73 | 163.8 | 0.81 | 0.38 | 0.22 | 0.38 | 0.40 |
| B3X2 | 0.73 | 150.0 | 0.44 | 0.53 | 0.22 | 0.73 | 0.51 |
| B3X4 | 0.59 | 110.0 | 1.20 | 0.77 | 0.29 | 0.77 | 1.05 |

TABLE 6-continued

Sorption experiments with aqueous solutions and pure alcohol.

100% isobutanol sorption

| Sample | $\phi_{PDMS}$ | $M_n$ (kg/mol) | 40° C. | 50° C. | 60° C. | 70° C. | 76° C. |
|---|---|---|---|---|---|---|---|
| B4X4 | 0.83 | 117.4 | 41.25 | unstable | unstable | unstable | unstable |
| B4X5 | 0.82 | 131.3 | 80.59 | unstable | unstable | unstable | unstable |
| B4X3 | 0.73 | 163.8 | 53.21 | 106.24 | unstable | unstable | unstable |
| B3X2 | 0.73 | 150.0 | 54.99 | 83.39 | unstable | unstable | unstable |
| B3X4 | 0.59 | 110.0 | 36.96 | 68.33 | 119.40 | unstable | unstable |

8% ethanol sorption

| Sample | $\phi_{PDMS}$ | $M_n$ (kg/mol) | 40° C. | 50° C. | 60° C. | 70° C. | 76° C. |
|---|---|---|---|---|---|---|---|
| B4X4 | 0.83 | 117.4 | 0.33 | 0.41 | 0.21 | 0.14 | −0.02 |
| B4X5 | 0.82 | 131.3 | 0.06 | 1.15 | 0.23 | 0.21 | −0.12 |
| B4X3 | 0.73 | 163.8 | 0.39 | 0.50 | 0.06 | 0.22 | 0.14 |
| B3X2 | 0.73 | 150.0 | 0.04 | 0.15 | 0.29 | 0.42 | 0.09 |
| B3X4 | 0.59 | 110.0 | 0.18 | 0.21 | −0.04 | 0.25 | 0.10 |

45% ethanol sorption

| Sample | $\phi_{PDMS}$ | $M_n$ (kg/mol) | 40° C. | 50° C. | 60° C. | 70° C. | 76° C. |
|---|---|---|---|---|---|---|---|
| B4X4 | 0.83 | 117.4 | 1.92 | 2.65 | 1.14 | 1.16 |
| B4X5 | 0.82 | 131.3 | 1.83 | 2.30 | 0.87 | 1.77 |
| B4X3 | 0.73 | 163.8 | 2.35 | 1.32 | 1.16 | 0.64 |
| B3X2 | 0.73 | 150.0 | 2.02 | 0.59 | 1.23 | 0.59 |
| B3X4 | 0.59 | 110.0 | 3.83 | 2.60 | 1.40 | 1.67 |

100% ethanol sorption

| Sample | $\phi_{PDMS}$ | $M_n$ (kg/mol) | 40° C. | 50° C. | 60° C. | 70° C. | 76° C. |
|---|---|---|---|---|---|---|---|
| B4X4 | 0.83 | 117.4 | 5.63 | | | | |
| B4X5 | 0.82 | 131.3 | 5.91 | | | | |
| B4X3 | 0.73 | 163.8 | 6.74 | | | | |
| B3X2 | 0.73 | 150.0 | 7.58 | | | | |
| B3X4 | 0.59 | 110.0 | 8.06 | | | | |

EXAMPLES

The following examples are offered to illustrate but not to limit the invention.

1. Polymerization

Polystyrene-b-polydimethylsiloxane-b-polystyrene (SDS) triblock copolymers are synthesized using living anionic polymerization to attain better control on the molecular weight and achieve low polydispersity. Cyclohexane, sec-butyl lithium ("s-BuLi"), dibutyl magnesium ("DBM"), calcium hydride ($CaH_2$), styrene, dichlorodimethylsilane ($SiMe_2Cl_2$), and digylme were purchased from Sigma-Aldrich and hexamethylcyclotrisiloxane monomer (D3) was obtained from Gelest. All the chemicals were purified by using high vacuum techniques unless otherwise stated.

Cyclohexane is purified by a commercial solvent purification system (Braun, MB AUTO-SPS Solvent Purification System) followed by stirring over polystyrl lithium anions overnight to remove trace amounts of moisture. Three freeze-thaw cycles were applied to remove the oxygen from the cyclohexane. Finally, cyclohexane was distilled into a flamed airfree reactor (where the reaction will be carried out) and taken to the glove box where the required amount of s-BuLi initiator and a stir bar is added.

The styrene monomer (typically 20-30% excess) is purified by stirring over a freshly powdered $CaH_2$ overnight at room temperature. Concurrently, a DBM solution is added to a flame-dried reactor, placed on the vacuum line, and dried. Styrene is distilled into the DBM reactor from the round bottom flask containing $CaH_2$ and stirred over dibutylmagnesium overnight at room temperature. Styrene from the DBM reactor is distilled into an ampoule and the ampoule is taken to the glovebox and styrene is added to the reactor containing cyclohexane and initiator. The polymerization is conducted in the glove box at room temperature for ~12 hours and a characteristic yellow "living" polymer mixture is retained during polymerization. An aliquot is then taken and terminated with degassed methanol or isopropanol for characterization using gel permeation chromatography (GPC) to determine its molecular weight.

Hexamethylcyclotrisiloxane ($D_3$) monomer, a solid at room temperature (m.p. is 50-64° C.), and an equal amount of cyclohexane from the solvent purification system were transferred into a round bottom flask with freshly powdered $CaH_2$ (cyclohexane as a solvent is used to avoid heating the $D_3$ monomer above its melting point to be able to be stirred with calcium hydride). Subsequently, an airfree adaptor was attached to the round bottom flask and the round bottom flask was attached to the vacuum line. The mixture was stirred at room temperature overnight to remove the moisture from the monomer and the solvent mixture. The solvent and monomer mixture was degassed via 3 freeze-thaw cycles to remove the trace amount of oxygen from the mixture. Next, $D_3$ monomer is purified with DBM using a similar procedure as described above for styrene. The $D_3$ monomer and cyclohexane were transferred to the DBM containing reactor via distillation of cyclohexane and sublimation of the $D_3$ monomer. Heating the $D_3$ monomer is necessary to provide the driving force for the sublimation of the $D_3$ monomer. Heating of the reactor and vacuum line is carried out using an oil bath (at 90° C.) and heating tapes, respectively (at 90° C.). The $D_3$ monomer and cyclohexane is stirred over DBM for 3 hours and then the purified monomer and solvent is transferred into a reactor as described above.

The reactor containing the purified D3 monomer and cyclohexane is transferred to the glove box and a pre-calculated amount of the D3/cyclohexane mixture is transferred to the reactor containing living polystyrl lithium chains using volumetric pipettes. The polymerization of D3 monomer does not take place, therefore a promoter, 2-methoxyethylether (diglyme) is added to the reaction mixture (≈5% v/v) to complex the lithium ions and facilitate the polymerization of D3 monomer. The co-polymerization mixture is allowed to stir for ~3-5 hours in the glove box. Use of diglyme as the promoter unexpectedly provides high molecular weight diblocks with high volume fraction of PDMS ($\phi$PDMS). The high molecular weight, high volume fraction PDMS diblocks are subsequently coupled to form the SDS triblock copolymers.

SDS triblock copolymers are obtained by introducing the coupling agent, dimethyldichlorosilane, in the glove box, and the polymerization mixture was allowed to stir until the completion of the coupling reaction.

At the end of the coupling reaction, degassed isopropanol is added into the reactor to terminate the uncoupled living ends, and the polymerization mixture precipitated in 50% v/v methanol and isopropanol mixture. SDS copolymers were collected via filtration and dried under vacuum until a constant weight is achieved.

Gas Permeation Measurements

Gas permeation measurements were performed on the in-house build constant-volume and variable pressure setup. The SDS membranes with thicknesses (1) of 150-200 μm were sandwiched between two aluminum tapes which have openings of a known area (A) allowing gas to permeate through membrane. After applying moderate vacuum (≈200 mtorr) to both sides of the membrane, the test gas was introduced at a known pressure on the upstream side of the membrane. The downstream pressure was recorded upon gas permeation through the SDS membrane. Since the downstream volume is known (V), the permeability (P) of individual gases can be calculated as following:

$$P = \frac{Vl}{ART\Delta p}\left(\frac{dp}{dt}\right)$$

where R is the universal gas constant, T is the absolute temperature, $\Delta p$ is the difference between upstream and downstream pressures, and dp/dt is the steady rate of pressure increase on the downstream side. The permeability of oxygen and carbon dioxide through SDS membranes were calculated for an upstream pressure of two atmospheres at 23° C.

Contact Angle Measurements

The contact angle measurements were performed using Rame-Hart contact angle goniometer (model 100-00) equipped with digital camera and image processing software. High purity deionized water was used as a probing liquid. The contact angles were recorded by dispensing 8 μl of liquid to obtain information about surface energy. The contact angle data are an average value for at least five different measurements that were performed across the sample surface with error in the range of ±2.0°.

Differential Scanning Calorimetry

Differential scanning calorimetry (DSC) sample analysis was performed using a TA Instruments Q2000 commercial system equipped with a liquid nitrogen (LN2) cooling system. The instrument was calibrated before the experiments. All experimental data were recorded according to a two-step cycling procedure to delete the thermal history of the copolymer films. First, samples were cooled from 25 to −150° C. with a rate of −5° C./min, and then held at −150° C. isothermally for 5 minutes. Then the temperature was increased to 150° C. with a rate of 5° C./min and kept at 150° C. isothermally for 5 minutes. The cooling and heating cycles were repeated one more time. The glass transition temperature (Tg) of SDS membranes was determined from the onset points of the thermograms and the Tg's from the 2nd heating thermograms were reported. A polydimethylsiloxane (PDMS) network prepared from α,ω-vinyl terminated PDMS (Gelest, 28 kg/mol) and tetrakisdimethylsiloxysilane in the presence of a platinum catalyst was used to determine the baseline Tg for comparison.

Thermo Gravimetric Analysis

The thermal stability of the SDS membranes was studied using a Thermo Gravimetric Analysis (TGA) on a TA Instruments Q500 setup. In order to study the thermo-oxidative degradation behavior of the SDS membranes, experiments were carried out under an oxygen atmosphere. All studies were performed from 25 to 900° C. in platinum pans with a heating rate of 10° C./min A polystyrene standard with a molecular weight of 131 kg/mol and PDI of 1.05 (Polymer Source) and the PDMS network were used to determine the thermo-oxidative stability of polystyrene and PDMS respectively as a benchmark.

Membrane Preparation

Thin membranes (150-200 μm) for pervaporation experiments were prepared by melt pressing the SDS polymers between PTFE sheets (5 mil thickness, McMaster) at 150° C. All the membranes were prepared as described below to obtain consistent thickness and microstructure (effect of annealing). One gram of SDS copolymer was weighed and the pieces of the copolymer were sandwiched between PTFE sheets. The sandwiched copolymer between PTFE sheets was placed between two steel plates and then melt pressed to obtain ≈150 μm films for pervaporation experiments. The resulting SDS copolymer film was punched with a circular punch to obtain a membrane with a diameter of 7.5 cm for pervaporation experiments.

Pervaporation Experiments

Pervaporation experiments of ethanol (8%, 45%, and 75% w/w), n-butanol (1% w/w) and isobutanol (1 and 2% w/w) in water were conducted on a laboratory bench test unit purchased from Sulzer Chemtech, Germany. The membrane was held inside a circular cell restrained with an o-ring, providing a total permeation area of 37 cm². The temperature of the feed was controlled in the range of 40 to 76° C. within ±0.1° C. using a temperature controller equipped with a single stage rotary vane pump for re-circulation of cooling water. Temperature of the feed liquid was also monitored at the inlet and outlet of the pervaporation cell with separate thermocouples. Each experiment began with approximately two liters of dilute alcohol-water solution in the feed tank. After starting the feed pump, the system was allowed to attain steady state for 1 hour before permeate samples were collected. On the permeate side of the membrane, a vacuum of −2-4 mbar was applied using a vacuum pump (Welch, model 2014) and permeates were condensed in a trap cooled with a dry-ice/isopropanol mixture at −70° C. For each polymer, two different membranes were prepared and tested with duplicate runs at all temperatures, and an average value has been reported. The standard deviation is taken to be the uncertainty of the measurements.

To measure the flux, permeate samples were weighed to determine the mass permeated through the membrane during the experiment. Both the feed and the permeate samples were analyzed using 1H NMR with deuterated acetone (acetone-d6) as the solvent to determine the compositions of ethanol and water. Feed composition changes only slightly for 8 and 45% ethanol solutions due to small amounts permeating through the membrane, and was taken to be the average of the compositions at the beginning and the end of permeate collection. On the other hand, the feed composition for dilute butanol feeds changed during the experiment due to a small amount of alcohol present in the system. Therefore, the calculated amount of butanol and isobutanol is added between the runs to compensate for the amount of alcohol removed due to pervaporation of alcohol through the membrane during the course of the experiment.

Overall flux, the total mass permeated through the membrane per unit area and time, was calculated according to equation 1:

$$J = \frac{M}{A\Delta\tau_C}, \qquad \text{Eq. 1}$$

where M is the total mass of the permeate collected, A is the permeation area (37 cm2) and $\Delta\tau C$ is the permeate collection time. The individual component fluxes, $J_i$, were calculated by the multiplication of the individual component concentrations by the overall flux J given by Eq. (1).

Membrane permeability is calculated according to equation 2:

$$J_i = \frac{P_i}{t}(x_i\gamma_i p_i^{sat} - y_i p_p), \qquad \text{Eq. 2}$$

where $P_i$ is the membrane permeability, t is the membrane thickness, $x_i$ is the feed mole fraction, $\gamma_i$ is the activity coefficient, $p_i^{sat}$ is saturated vapor, pressure, $y_i$ is the permeate mole fraction and $p_p$ is the permeate pressure. The activity coefficients were calculated using the Van Laar equation and the saturated vapor pressure $p_i^{sat}$ was determined using the Antoine equation. The membrane separation factor is determined according to equation 3:

$$M_{SF} = \frac{P_{ethanol}}{P_{water}}, \qquad \text{Eq. 3}$$

where $P_{ethanol}$ and $P_{water}$ are permeabilities of ethanol and water respectively, calculated on a mass basis.

Although the methods and compositions described herein have been described in connection with some embodiments, it is not intended to be limited to the specific form set forth herein. Rather, the scope of the methods and compositions described herein is limited only by the claims. Additionally, although a feature may appear to be described in connection with particular embodiments, one skilled in the art would recognize that various features of the described embodiments may be combined in accordance with the methods and compositions described herein.

Furthermore, although individually listed, a plurality of means, elements or method steps may be implemented by, for example, a single method. Additionally, although individual features may be included in different claims, these may be advantageously combined, and the inclusion in different claims does not imply that a combination of features is not feasible and/or advantageous. Also, the inclusion of a feature in one category of claims does not imply a limitation to this category, but rather the feature may be equally applicable to other claim categories, as appropriate.

Terms and phrases used in this document, and embodiments thereof, unless otherwise expressly stated, should be construed as open ended as opposed to limiting. As examples of the foregoing: the term "including" should be read to mean "including, without limitation" or the like; the terms "example" or "some embodiments" are used to provide exemplary instances of the item in discussion, not an exhaustive or limiting list thereof; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of methods and compositions described herein may be described or claimed in the singular, the plural is contemplated to be within the scope thereof unless limitation to the singular is explicitly stated. The presence of broadening words and phrases such as "one or more," "at least," "but not limited to," "in some embodiments" or other like phrases in some instances shall not be read to mean that the narrower case is intended or required in instances where such broadening phrases may be absent.

In addition, while compositions and methods described herein may be open to inclusion of additional unrecited features, and thus may be described or claimed as 'comprising' the specified features, a composition or process consisting only of the recited features, or consisting essentially of the recited features is expressly within the scope of the invention as well.

We claim:

1. A poly(styrene-b-dialkylsiloxane-b-styrene) triblock copolymer comprising a polydialkylsiloxane block and polystyrene end blocks,
   wherein the triblock copolymer has (i) a molecular weight in the range of about 110 kg/mol to about 1000 kg/mol, and (ii) cylindrical morphology, lamellar morphology, double diamond morphology, or gyroid morphology;
   and wherein the triblock copolymer loses about 5% of weight at a temperature in the range of about 290° C. to about 350° C.

2. The triblock copolymer of claim 1, wherein the triblock copolymer has a molecular weight in the range of about 120 kg/mol to about 1000 kg/mol.

3. The triblock copolymer of claim 1, wherein the triblock copolymer has a molecular weight in the range of about 120 kg/mol to about 300 kg/mol.

4. The triblock copolymer of claim 1, wherein the triblock copolymer has a molecular weight in the range of about 130 kg/mol to about 300 kg/mol.

5. The triblock copolymer of claim 1, wherein the triblock copolymer has a domain spacing (d) in the range of about 20 to about 90 nanometers.

6. The triblock copolymer of claim 1, wherein the polydialkylsiloxane is polydimethylsiloxane.

7. The triblock copolymer of claim 1, wherein the polydialkylsiloxane block has a volume fraction of about 0.6 to about 0.95 relative to the polystyrene end blocks.

8. A method of selectively separating an alcohol from an aqueous mixture, the method comprising:
   contacting the aqueous mixture with a membrane comprising a poly(styrene-b-dialkylsiloxane-b-styrene) triblock copolymer;
     wherein the poly(styrene-b-dialkylsiloxane-b- styrene) triblock copolymer comprises a polydialkylsiloxane block and polystyrene end blocks, wherein the triblock copolymer has (i) a molecular weight in the range of about 110 kg/mol to about 1000 kg/mol, and (ii) cylindrical morphology, lamellar morphology, double diamond morphology, or gyroid morphology; and
   whereby the alcohol selectively permeates through the membrane to form a permeate comprising the alcohol at a concentration greater than the concentration of the alcohol of the aqueous mixture.

9. The method of claim 8, wherein the membrane has a separation factor ($M_{SF}$) in the range of about 1.0 to 4.0.

10. The method of claim 8, wherein the alcohol is selected from the group consisting of ethanol, n-butanol, isobutanol, 2-butanol, 1-pentanol, 1-hexanol, 1-heptanol, 1-octanol, 1-nonanol, and 1-decanol.

11. A membrane comprising the triblock copolymer of claim 1.

12. A method of selectively separating one or more organic compounds from an aqueous mixture, the method comprising:
   contacting the aqueous mixture with a membrane comprising a poly(styrene-b-dialkylsiloxane-b-styrene) triblock copolymer;
     wherein the poly(styrene-b-dialkylsiloxane-b-styrene) triblock copolymer comprises a polydialkylsiloxane block and polystyrene end blocks, wherein the triblock copolymer has (i) a molecular weight in the range of about 110 kg/mol to about 1000 kg/mol, and (ii) cylindrical morphology, lamellar morphology, double diamond morphology, or gyroid morphology; and
   whereby the one or more organic compounds selectively permeates through the membrane to form a permeate comprising the one or more organic compounds at a concentration greater than the concentration of the one or more organic compounds of the aqueous mixture.

13. The method of claim 12, wherein the one or more organic compounds is selected from the group consisting of acetone, ethanol, n-butanol, isobutanol, 2-butanol, 1-pentanol, 1-hexanol, 1-heptanol, 1-octanol, 1-nonanol, 1-decanol, acetic acid, formic acid, levulinic acid, succinic acid, furfural, 5-hydroxymethylfurfural, 2-furoic acid, vanillic acid, ferulic acid, p-coumaric acid, syringic acid (4-hydroxy-3,5-dimethoxybenzoic acid), 4-hydroxybenzoic acid, protocatechuic acid (3,4-dihydroxybenzoic acid), homovanillic acid (2-(4-hydroxy-3-methoxy-phenyl)acetic acid), caffeic acid (3,4-dihydroxycinnamic acid), sinapic acid, propionic acid, vanillylmandelic acid, 4-hydroxymandelic acid, 4-hydroxyphenylacetic acid, 3-hydroxybenzoic acid, 2,5-dihydroxybenzoic acid, benzoic acid, vanillian, syringaldehyde, 4-hydroxybenzaldehyde, coniferyl aldehyde (4-OH-3-OCH$_3$-cinnamaldehyde), sinapinaldehyde (3,5-dimethoxy-4-hydroxycinnamaldehyd), protocatechualdehyde (3,4-dihydroxybenzaldehyde), acetovanillone (4'-hydroxy-3'-methoxyacetophenone), acetosyringone (3',5'-dimethoxy-4'-hydroxyacetophenone), guaiacol, coniferyl alcohol (4-(3-hydroxy-1-propenyl)-2-methoxyphenol), hydroquinone, catechol (pyrocatechol), vanillyl alcohol (4-hydroxy-3-methoxybenzyl alcohol), eugenol, and mixtures of any combination thereof.

14. The method of claim 12, wherein the one or more organic compounds is selected from the group consisting of acetone, ethanol, n-butanol, isobutanol, 2-butanol, 1-pentanol, 1-hexanol, 1-heptanol, 1-octanol, 1-nonanol, 1-decanol, and mixtures of any combination thereof.

15. The method of claim 12, wherein the one or more organic compounds is selected from the group consisting of acetic acid, formic acid, levulinic acid, succinic acid, furfural, 5-hydroxymethylfurfural, and mixtures of any combination thereof.

16. The method of claim 12, wherein the aqueous mixture is an acetone-n-butanol-ethanol (ABE) fermentation mixture.

17. The method of claim 12, wherein the one or more organic compounds is selected from the group consisting of acetone, n-butanol, ethanol, and mixtures of any combination thereof.

18. The method of claim 12, wherein the triblock copolymer loses about 5% of weight at a temperature in the range of about 290° C. to about 350° C.

19. The method of claim 12, wherein the triblock copolymer has a molecular weight in the range of about 120 kg/mol to about 300 kg/mol.

20. The method of claim 12, wherein the triblock copolymer has a domain spacing (d) in the range of about 20 to about 90 nanometers.

21. The method of claim 12, wherein the polydialkylsiloxane block has a volume fraction of about 0.6 to about 0.95 relative to the polystyrene end blocks.

22. The method of claim 8, wherein the triblock copolymer loses about 5% of weight at a temperature in the range of about 290° C. to about 350° C.

23. The method of claim 8, wherein the triblock copolymer has a molecular weight in the range of about 120 kg/mol to about 300 kg/mol.

24. The method of claim 8, wherein the triblock copolymer has a domain spacing (d) in the range of about 20 to about 90 nanometers.

25. The method of claim 8, wherein the polydialkylsiloxane block has a volume fraction of about 0.6 to about 0.95 relative to the polystyrene end blocks.

* * * * *